(12) United States Patent
Xu et al.

(10) Patent No.: US 8,987,288 B2
(45) Date of Patent: Mar. 24, 2015

(54) HETEROCYCLIC AMINOBERBAMINE DERIVATIVES, THE PREPARATION PROCESS AND USE THEREOF

(75) Inventors: Rongzhen Xu, Hangzhou (CN); Fuwen Xie, Long Yan (CN); Hongxi Lai, Long Yan (CN); Frank Rong, Hangzhou (CN)

(73) Assignee: Hangzhou Bensheng Pharmaceutical Co., Ltd., Hangzhou, Zhejiang (CN)

( * ) Notice: Subject to any disclaimer, the term of this patent is extended or adjusted under 35 U.S.C. 154(b) by 192 days.

(21) Appl. No.: 13/821,667

(22) PCT Filed: Sep. 9, 2011

(86) PCT No.: PCT/CN2011/079501
§ 371 (c)(1),
(2), (4) Date: Mar. 8, 2013

(87) PCT Pub. No.: WO2012/031563
PCT Pub. Date: Mar. 15, 2012

(65) Prior Publication Data
US 2013/0178470 A1    Jul. 11, 2013

(30) Foreign Application Priority Data
Sep. 10, 2010    (WO) ............... PCT/CN2010/076792

(51) Int. Cl.
| C07D 491/056 | (2006.01) |
| A61K 31/535 | (2006.01) |
| A61K 31/4965 | (2006.01) |
| A61K 31/505 | (2006.01) |
| A61K 31/44 | (2006.01) |
| A61K 31/4738 | (2006.01) |
| C07D 491/18 | (2006.01) |

(52) U.S. Cl.
CPC ........ *C07D 491/056* (2013.01); *A61K 31/4738* (2013.01); *C07D 491/18* (2013.01)
USPC ............... 514/279; 514/232; 514/8; 514/275; 514/255.05; 544/120; 544/331; 544/405; 546/35

(58) Field of Classification Search
CPC ............. C07D 491/056; A61K 31/535; A61K 31/4965; A61K 31/505; A61K 31/44
USPC .......... 514/232.8, 279, 275, 255.05; 544/120, 544/331, 405; 546/35
See application file for complete search history.

(56) References Cited

U.S. PATENT DOCUMENTS

2010/0298369 A1    11/2010    Horne et al.

FOREIGN PATENT DOCUMENTS

| CN | 1810247 | 8/2006 |
| CN | 101273989 | * 10/2008 |
| EP | 2610257 A1 | 7/2013 |
| JP | 3002183 A | 1/1991 |
| JP | 2627666 B2 | 7/1997 |

OTHER PUBLICATIONS

J.W. Xie "Design, Synthesis and Biological Evaluation of Indolin-2-one and Berbamine Derivatives", Chinese doctoral Dissertations, Full-text Database, Medicine and Health Sciences, 2009, No. 10, pp. 174-183, Oct. 15, 2009.
Gong et al., "Inhibition of Four Berbamine Derivative toward Activity of Calmodulin-induced Myosin Light Chain Kinase", J. China Pharmaceutical University, 1991, vol. 22, No. 2, pp. 93-96.
International Search Report of PCT/CN2011/079501 mailed Dec. 15, 2011 (English translation).
Xie J, et al., Berbamine derivatives: A novel class of compounds for anti-leukemia activity. European Journal of Medicinal Chemistry. 2009, 44:3293-3298.
Szewczyk JW., et al., SAR studies: Designing potent amd selective LXR agonists. Biorganic & Medicinal Chemistry Letters. 2006, 16:3055-3060.

* cited by examiner

*Primary Examiner* — James O Wilson
*Assistant Examiner* — Ebenezer O Sackey
(74) *Attorney, Agent, or Firm* — McCarter & English, LLP; Steven G. Davis

(57) ABSTRACT

The present invention relates to a novel berbamine derivative of formula I or a pharmaceutically acceptable salt thereof, a process for preparation of the same, a pharmaceutical composition comprising said compound and its use in manufacture of an antitumor medicament.

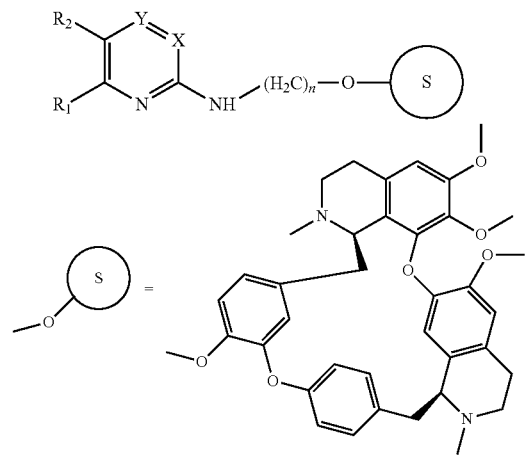

Formula (I)

27 Claims, No Drawings

HETEROCYCLIC AMINOBERBAMINE DERIVATIVES, THE PREPARATION PROCESS AND USE THEREOF

RELATED APPLICATIONS

This application is a 35 U.S.C. §371 national stage filing of International Application No. PCT/CN2011/079501, filed Sep. 9, 2011, which, in turn, claims priority to International Application No. PCT/CN2010/076792, filed Sep. 10, 2010.

TECHNICAL FIELD

The present invention belongs to the fields of natural medicine and pharmaceutical chemistry, and relates to heterocyclic amino berbamine derivatives, to a process for the preparation of these compounds, compositions containing such compounds and their use in preparing antineoplastic medicaments.

BACKGROUND OF THE INVENTION

Berbamine (BBM), also known as 6,6',7-trimethoxy-2,2'-dimethylberbaman-12-ol, is a bi-benzyl isoquinoline alkaloid extracted from Chinese herbal plants of berberis. Due to its biological activities, many researchers are attracted to conduct extensive investigations on berbamine itself and its analogues.

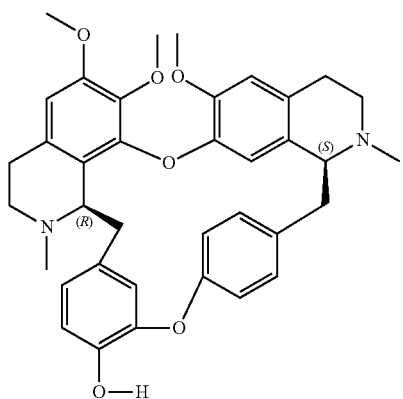

Berbamine

CAS: 478-61-5

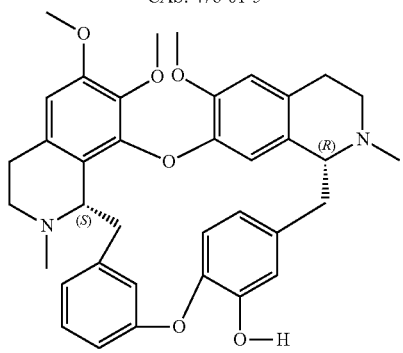

Oxyacanthine

CAS: 15352-74-6

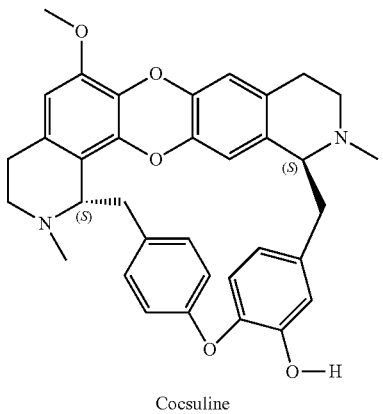

Cocsuline

CAS: 26279-88-9

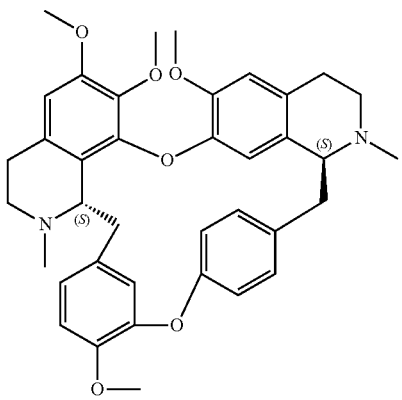

Tetrandrine

CAS: 518-34-3

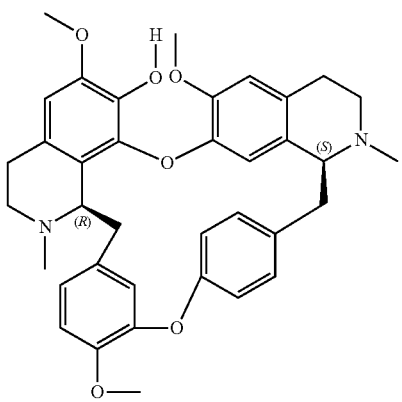

Fangchinoline

CAS: 436-77-1

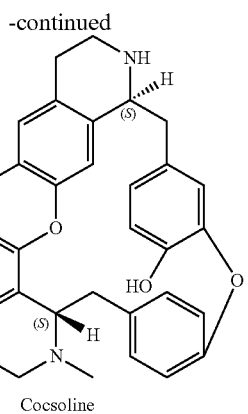

Cocsoline
CAS: 54352-70-4

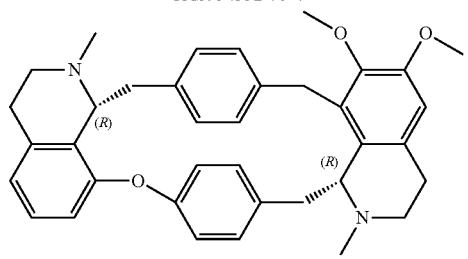

Cycleanine
Mol. Wt.: 560.73
CAS: 518-94-5

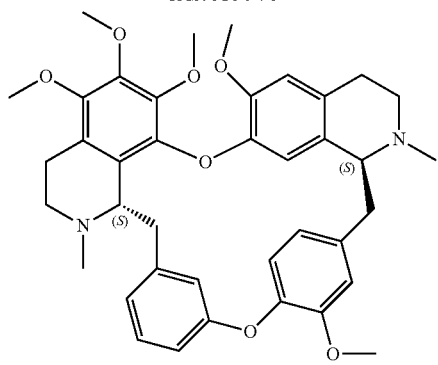

Thalrugosaminine
Mol. Wt.: 652.78
CAS: 22226-73-9

Berbamine and its Analogues

Berbamine has the effect of stimulating myeloid cell proliferation, improving the level of hematopoietic stem cell colony stimulating factor (GCSF), promoting the proliferation of bone marrow hematopoietic stem cells and myeloid progenitor cells and their differentiation to granulocytes, and promoting the proliferation of leukocytes [LIN Chuanrong, et al., The clinical observations on the treatment of chemotherapy-induced leukopenia with Shengbei'an (berbamine), *Prepared Chinese Medicine*, 1994, 16 (7); 29].

Berbamine inhibits the proliferation of prostate cancer PC-3 cells by introducing apoptosis and influencing the cell cycles in a time- and concentration-dependent manner [SUN Peng, el al., The effect of berbamine inducing apoptosis of prostate cancer PC-3 cells and the mechanism, *Chinese Journal of Experimental Surgery*, 2007, 24 (8): 957].

Berbamine exhibits obvious proliferation inhibition and clear apoptosis induction effects on the K562 cells in vitro, and has a time-concentration dependent relationship. In bodies of the tumor-bearing nude mice, berbamine also has significant inhibition effect on K562 cell growth, in particular can down-regulate the expression level of bcr/abl mRNA in tumor tissue cells [Wu Dong, el al., The experimental study of the actions of berbamine on K562 cells in vitro and in vivo, *Journal of Chinese Experimental Hematology*, 2005, 13 (3): 373].

Berbamine has effect of inhibiting cytotoxic T lymphocytes, and significantly promoting mice natural killer cell activity in vitro, and can induce relative high level of interleukin II (IL-2) in vitro and in vivo and avoid the toxic and adverse effects induced by large doses of IL-2 for treatment of tumor. It is demonstrated experimentally that berbamine has a good protective effect for immune system in mice against radiation damage [LIU Xin, el al., The immune regulation action of berbamine on BALB/C mice, *Journal of China Medical University*, 1996, 25 (3): 229; LUO Chongnian, et al., The inhibition of berbamine on mice splenocytes cytotoxic T lymphocyte activity, *Chinese Journal of Pharmacology and Toxicology*, 1995, 9 (2): 159-160; G E Mingzhu, et al., The experimental study of immune protection action of berbamine on irradiated mice, *Journal of Immunology*, 1998, 14 (4): 238].

There are the studies and reports on the mechanism of berbamine inducing apoptosis of human leukemia Jurkat cells as well. The results show that, berbamine can selectively inhibit the apoptosis of human leukemia Jurkat cells, make the cell cycle arrested in S phase, and increase the caspase-3 protein expression of the cells. And as the increase of drug concentration from 0.5 ug/mL to 10 ug/mL, the cell viability rate was reduced from 93.69% to 14.85%, and berbamine in this action concentration range was found having no obvious cytotoxicity on normal human peripheral blood leucocytes [DONG Zhiyu, et al., The experimental study of berbamine on inducing apoptosis of human leukemia Jurkat cells, *Chinese Tumor*, 2007, 16 (9): 72].

Berbamine hydrochloride tablet has been approved for marketing in China, and is used for treating leukopenia of various causes, including prevention of leukocytopenia after radiotherapy or chemotherapy of cancer.

There are also reports about the inhibiting effect of berbamine on cell proliferation. For example, berbamine and some of berbamine derivatives have significant inhibiting effect on brain malignant glioma cells, human cervical carcinoma cells, ascites carcinoma cells and melanoma cells [ZHANG Jinhong, et al, The influence of the structures of the berbamine and its derivatives on cervical carcinoma (CHeLa) cells proliferation, *Acta Scientiarum Naturalium University Nankaiensis*, 1996, 29 (2): 89; ZHANG Jinhong, et al., The influence of the berbamine and its derivatives on malignant melanoma cell proliferation, *Chinese Herbal Medicine*, 1997, 28 (8): 483; ZHANG Jinhong, et al., The preliminary exploration of the in vivo antitumor effect of the berbamine derivatives (EBB), *Chinese Herbal Medicine*, 1998, 29 (4): 243; DUAN Jiangyan et al., The influence of berbamine compounds on calmodulin protein level within melanoma cells, *Chinese Herbal Medicine*, 2002, 33 (1): 59]. [O-(4-ethoxy)-butyl]-berbamine (EBB) is a highly specific CaM antagonist, with a specific coefficient of 6.5 times higher than that of berbamine. EBB induces apoptosis of lung cancer cells and maintains the normal cell biological functions of main organs at the same time [DUAN Jiangyan, et al. The preliminary exploration of [O-(4-ethoxy)-butyl]-berbamine for induction of lung cancer cell apoptosis. *Journal of Shanxi Normal University (NATURAL SCIENCE EDITION)*, 2001, 15 (4): 55]. Another berbamine derivative is O-Dansyl berbamine (DB)

which comprises a hydrophobic fluorescent moiety. DB exhibits the inhibitory activity on the red cell membrane CaM-independent $Ca^{2+}+Mg^{2+}$ ATPase that was 25 times stronger than that of berbamine. DB has a significant inhibitory effect on intracellular granzyme phosphodiesterase activity, and there was an association between the dose and the activity. In addition, it was also found that the effect of DB on lung cancer cells was stronger than that of berbamine, whereas the toxicity of DB on human embryonic lung cell was lower than that of berbamine, The inhibition of DB on lung cancer cells is not only related to the inhibition of oncogene, but also related to the control of the inactivated tumor suppressor genes [ZHANG Jinhong, et al., The influence of the calmodulin antagonist O-Dansyl berbamine on phosphodiesterase and pulmonary cell proliferation, *Acta Scientarium Naturalium University Nankaiensis*, 2001, 34 (3): 64].

The inventors have demonstrated in their previous studies that the small molecule compound berbamine has obvious anti-leukemia effect (Leukemia Research. 2006, 30: 17-23).

In the patent CN 101273989A, the inventors have described the use of a class of berbamine derivatives, mainly the benzoyl and benzyl derivatives, in preparation of antitumor drugs.

So far, the reported compounds can only transiently inhibit tumor cell growth, but cannot completely removed the tumor, especially hematological malignancies such as leukemia, multiple myeloma and lymphoma, and solid tumors such as liver cancer, lung cancer, breast cancer, prostate cancer, osteosarcoma and the like. Obviously, the research and development of berbamine derivatives with higher antitumor activities are still to be conducted.

SUMMARY OF THE INVENTION

One object of the present invention is to provide novel berbamine derivatives of formula (I):

Formula (I)

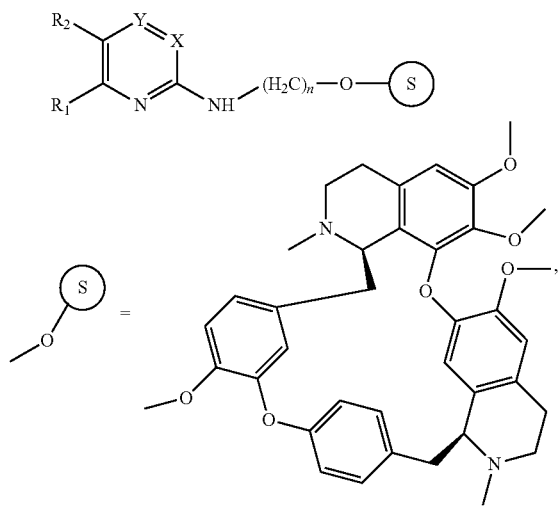

wherein
n=1-15;
$R_1$ is selected from H, $C_1$-$C_6$ alkoxy, halogenated $C_1$-$C_6$ alkoxy, $C_1$-$C_6$ alkylthio, halogenated $C_1$-$C_6$ alkylthio, $C_1$-$C_6$ alkyl, halogenated $C_1$-$C_6$ alkyl, $C_3$-$C_7$ cycloalkyl, halogenated $C_3$-$C_7$ cycloalkyl, halogen, nitro, cyano and amino optionally substituted with one or two $C_1$-$C_6$ alkyl;

$R_2$ is aryl carbamoyl, aryl carbonyl amino, heteroaryl carbamoyl, heteroaryl carbonyl amino, or N-linked nitrogen-containing heterocycle-carbonyl optionally substituted with a substituted selected from $C_1$-$C_6$ alkoxy, halogenated $C_1$-$C_6$ alkoxy, $C_1$-$C_6$ alkylthio, halogenated $C_1$-$C_6$ alkylthio, $C_1$-$C_6$ alkyl, halogenated $C_1$-$C_6$ alkyl, $C_3$-$C_7$ cycloalkyl, halogenated $C_3$-$C_7$ cycloalkyl, hydroxyl, halogen, nitro, cyano and amino optionally substituted with one or two $C_1$-$C_6$ alkyl;

X and Y are independently absent, CH, N or S, provided that X and Y are not be absent at the same time; or a pharmaceutically acceptable salt thereof.

Another object of the present invention is to provide a process for preparing the compound of formula (I);

(scheme 1)

wherein the target compound of formula (I) is prepared by conducting an animation reaction of a compound of formula (II) wish a compound of formula (III), wherein the n, X, Y, $R_1$ and $R_2$ in the compounds of formula (II) and (III) are defined same as in formula (I) above.

The compound of formula (II) is prepared by conducting a nucleophilic substitution reaction of a compound of formula (IV)/(IV') with a compound of formula (V)/(V').

(scheme 2)

wherein X, Y, $R_1$ and $R_2$ in the compounds of formula (I)), (IV) and (IV') are defined same as in formula (I) above.

Wherein the compound of formula (V) is preferably aryl amine, heteroaryl amine or nitrogen-containing heterocycle optionally substituted with a substitutent selected from $C_1$-$C_6$ alkoxy, halogenated $C_1$-$C_6$ alkoxy, $C_1$-$C_6$ alkylthio, halogenated $C_1$-$C_6$ alkylthio, $C_1$-$C_6$ alkyl, halogenated $C_1$-$C_6$ alkyl, $C_3$-$C_7$ cycloalkyl, halogenated $C_3$-$C_7$ cycloalkyl, hydroxyl, halogen, nitro, cyano and amino optionally substituted with one or two $C_1$-$C_6$ alkyl.

The compound of formula (V') is aryl formyl halide, heteroaryl formyl halide, or N-linked nitrogen-containing heterocycle-formyl halide optionally substituted with a substitutent selected from $C_1$-$C_6$ alkoxy, halogenated $C_1$-$C_6$ alkoxy, $C_1$-$C_6$ alkylthio, halogenated $C_1$-$C_6$ alkylthio, $C_1$-$C_6$ alkyl, halogenated $C_1$-$C_6$ alkyl, $C_3$-$C_7$ cycloalkyl, halogenated $C_3$-$C_7$ cycloalkyl, hydroxyl, halogen, nitro, cyano and amino optionally substituted with one or two $C_1$-$C_6$ alkyl.

The compound of formula (IV) is prepared by a halogen displacement reaction of the hydroxyl group of a carboxyl group between the compound of formula (VI) and the compound of formula (VII).

(scheme 3)

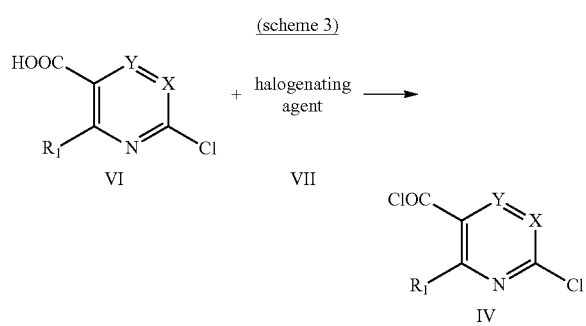

wherein X, Y, and $R_1$ in the compounds of formula (VI) and (IV) are defined same as in formula (I) above.

The halogenating agent of formula (VII) may be, but not limited to, phosphorus oxychloride ($POCl_3$), sulfoxide chloride ($SOCl_2$), or oxalyl chloride (($COCl)_2$).

Still another object of the present invention is to provide a pharmaceutical composition comprising the compound of the present invention, the said pharmaceutical composition comprising at least one compound of the present invention and optionally a pharmaceutically acceptable excipient.

Still another object of the present invention is to provide use of a compound of the present invention or a pharmaceutical composition comprising the same in manufacture of a medicament, especially an antitumor medicament. Accordingly, the present invention provides a method for treating patient suffering from a tumor, comprising administrating to the patient in need of thereof an therapeutically effective amount of at least one compound of the present invention. The said tumor is particularly selected from leukemia, multiple myeloma, lymphoma, liver cancer, gastric cancer, breast cancer, cholangiocellular carcinoma, pancreatic cancer, lung cancer, carcinoma of large intestine, osteosarcoma, melanoma, prostate cancer, and the like.

The preset invention also relates to the compound of the present invention for treating a tumor.

DETAILED DESCRIPTION OF THE INVENTION

The present invention provides the berbamine derivatives of formula (I)

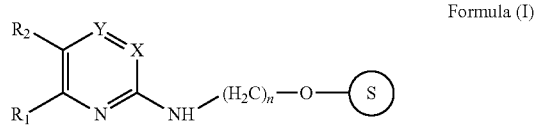

Formula (I)

-continued

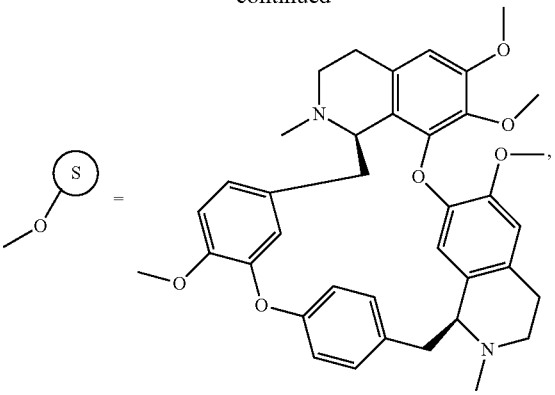

wherein, n=1-15;

$R_1$ is selected from H, $C_1$-$C_6$ alkoxy, halogenated $C_1$-$C_6$ alkoxy, $C_1$-$C_6$ alkylthio, halogenated $C_1$-$C_6$ alkylthio, $C_1$-$C_6$ alkyl, halogenated $C_1$-$C_6$ alkyl, $C_3$-$C_7$ cycloalkyl, halogenated $C_3$-$C_7$ cycloalkyl, halogen, nitro, cyano and amino optionally substituted with one or two $C_1$-$C_6$ alkyl;

$R_2$ is selected from aryl carbamoyl, aryl carbonyl amino, heteroaryl carbamoyl, heteroaryl carbonyl amino, N-linked nitrogen-containing heterocycle-carbonyl optionally substituted with a substituted selected from $C_1$-$C_6$ alkoxy, halogenated $C_1$-$C_6$ alkoxy, $C_1$-$C_6$ alkylthio, halogenated $C_1$-$C_6$ alkylthio, $C_1$-$C_6$ alkyl, halogenated $C_1$-$C_6$ alkyl, $C_3$-$C_7$ cycloalkyl, halogenated $C_3$-$C_7$ cycloalkyl, hydroxyl, halogen, nitro, cyano and amino optionally substituted with one or two $C_1$-$C_6$ alkyl;

X and Y are absent, CH, N or S, provided that X and Y cannot be absent at the same time; or a pharmaceutically acceptable salt thereof.

In one embodiment, the present invention relates to a compound of formula I, wherein n is an integer of 1-10.

In one embodiment, the present invention relates to a compound of formula I, wherein n is an integer of 1-7.

In one embodiment, the present invention relates to a compound of formula I, wherein n is an integer of 3-5, for example, n is 3, 4 or 5.

In one embodiment, the present invention relates to a compound of formula I, wherein $R_1$ is H, $C_1$-$C_6$ alkoxy, $C_1$-$C_6$ alkylthio, $C_1$-$C_6$ alkyl, $C_3$-$C_7$ cycloalkyl, halogen, nitro, cyano and amino optionally substituted with one or two $C_1$-$C_6$ alkyl.

In one embodiment, the present invention relates to a compound of formula I, wherein $R_1$ is H, $C_1$-$C_6$ alkoxy, $C_1$-$C_6$ alkyl, $C_3$-$C_7$ cycloalkyl or halogen.

In one embodiment, the present invention relates to a compound of formula I, wherein $R_1$ is H, $C_1$-$C_3$ alkoxy, $C_1$-$C_3$ alkyl, or $C_5$-$C_6$ cycloalkyl.

In one embodiment, the present invention relates to a compound of formula I, wherein $R_1$ is H, methoxy, or methyl.

In one embodiment, the present invention relates to a compound of formula I, wherein $R_1$ is methyl.

In one embodiment, the present invention relates to a compound of formula I, wherein $R_1$ is H.

In one embodiment, the present invention relates to a compound of formula I, wherein $R_2$ is aryl carbamoyl, aryl carbonyl amino, heteroaryl carbamoyl, heteroaryl carbonyl amino, N-linked nitrogen-containing heterocycle-carbonyl optionally substituted with a substitute selected from $C_1$-$C_6$ alkoxy, $C_1$-$C_6$ alkylthio, $C_1$-$C_6$ alkyl, $C_3$-$C_7$ cycloalkyl, hydroxyl, halogen, nitro, cyano and amino optionally substituted with one or two $C_1$-$C_6$ alkyl.

In one embodiment, the present invention relates to a compound of formula I, wherein $R_2$ is aryl carbamoyl, aryl carbonyl amino, heteroaryl carbamoyl, heteroaryl carbonyl amino, N-linked nitrogen-containing heterocycle-carbonyl optionally substituted with a substitutent selected from $C_1$-$C_3$ alkoxy, $C_1$-$C_3$ alkyl, $C_5$-$C_6$ cycloalkyl, hydroxyl, halogen, nitro, cyano and amino optionally substituted with one or two $C_1$-$C_3$ alkyl.

In one embodiment, the present invention relates to a compound of formula I, wherein $R_2$ is aryl carbamoyl, aryl carbonyl amino, heteroaryl carbamoyl, heteroaryl carbonyl amino, or N-linked nitrogen-containing heterocycle-carbonyl optionally substituted with a substitutent selected from $C_1$-$C_3$ alkoxy and halogen.

In one embodiment, the present invention relates to a compound of formula I, wherein $R_2$ is aryl carbamoyl, aryl carbonyl amino, heteroaryl carbamoyl, heteroaryl carbonyl amino, N-linked nitrogen-containing heterocycle-carbonyl optionally substituted with a substituted selected from methoxy, Cl and F.

In one embodiment, the present invention relates to a compound of formula I, wherein $R_2$ is phenyl carbamoyl, phenyl carbonyl amino, morpholin-4-yl carbonyl optionally substituted with a substitutent selected from methoxy, Cl and F.

In one embodiment, the present invention relates to a compound of formula I, wherein X=N, and Y=CH.

In one embodiment, the present invention relates to a compound of formula I, wherein X=S, and Y is absent.

In one embodiment, the present invention relates to a compound of formula I, wherein X=CH, and Y=N.

In one embodiment, the present invention relates to a compound of formula I, wherein X=CH, and Y=CH. The various preferable conditions in various embodiments of the present invention may be optionally combined as acceptable chemically.

In another embodiment, the present invention particularly preferably relates to the following compound of formula I:

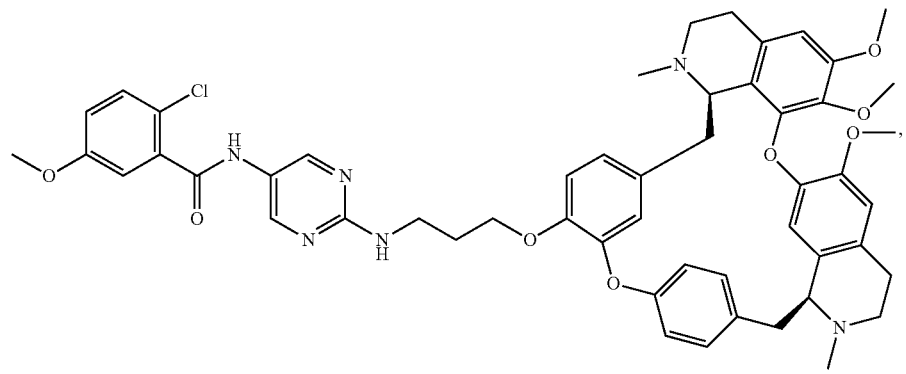

12-O-(3-(5-(2-chloro-5-methoxy-benzoylamino)-pyrimidin-2-amino)-propyl)-berbamine (compound(1))

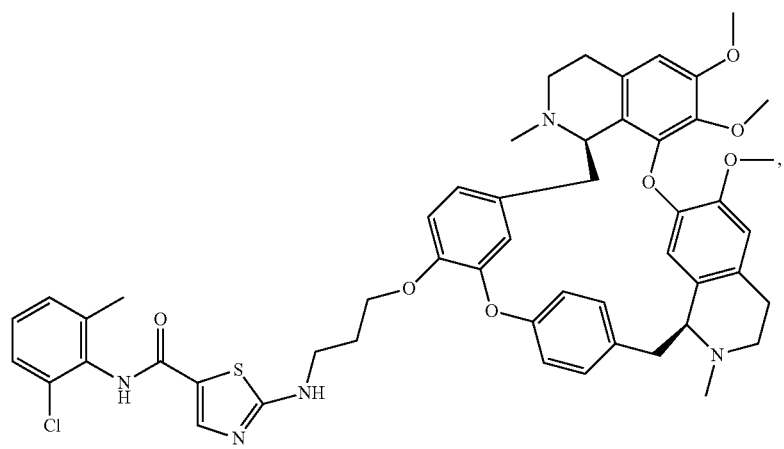

12-O-(3-(5-(2-chloro-6-methyl-carbaniloyl)-thiazol-2-amino)-propyl)-berbamine (compound(2))

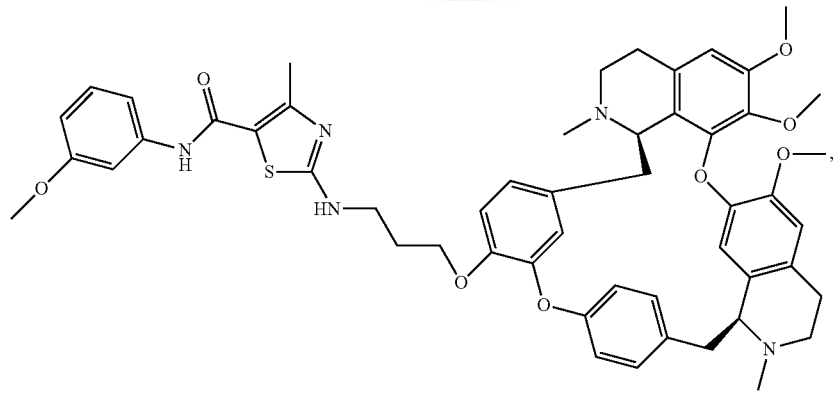
12-O-(3-(5-(3-methoxy-carbaniloyl)-4-methyl-thiazol-2-amino)-propyl)-berbamine (compound(3))
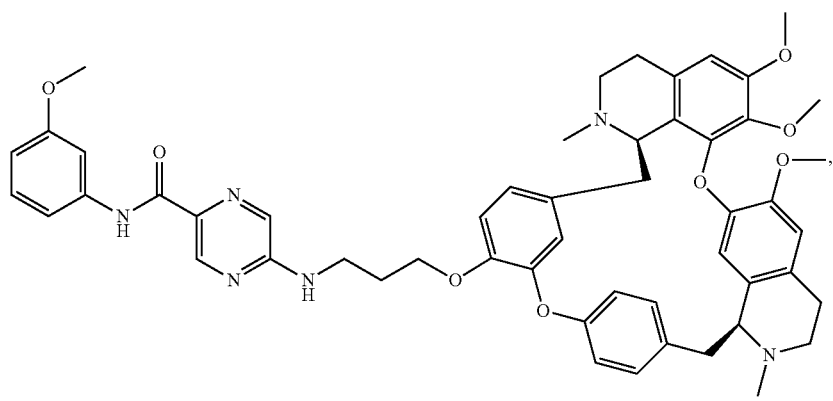
12-O-(3-(5-(3-methoxy-carbaniloyl)-pyrazin-2-amino)-propyl)-berbamine (compound(4))
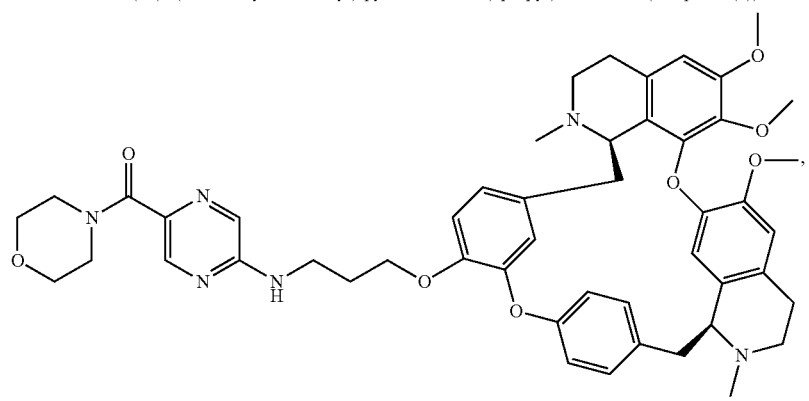
12-O-(3-(5-(morpholin-4-formyl)-pyrazin-2-amino)-propyl)-berbamine (compound(5))
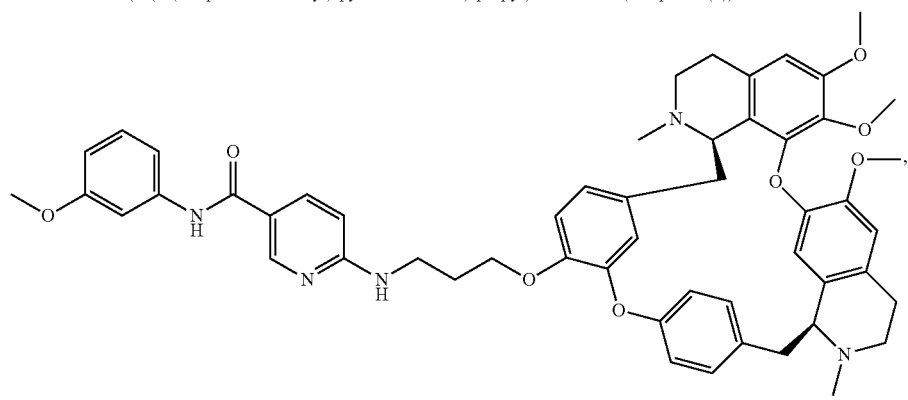
12-O-(3-(5-(3-methoxy-carbaniloyl)-pyridin-2-amino)-propyl)-berbamine (compound(6))

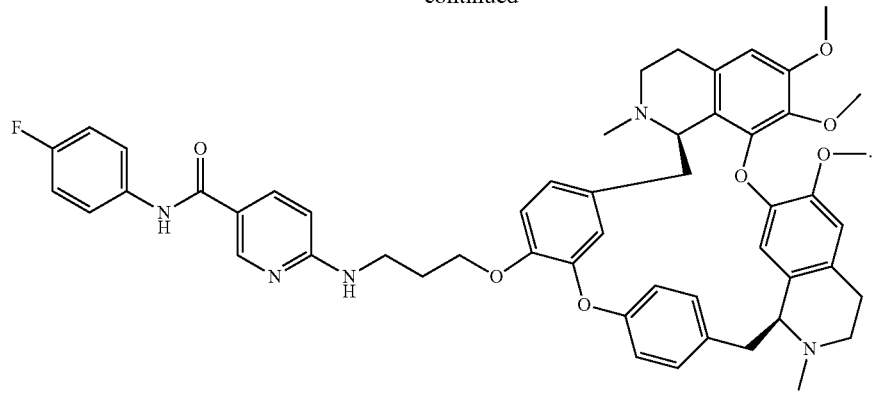

12-O-(3-(5-(4-fluorophenyl-carbamoyl)-pyridin-2-amino)-propyl)-berbamine (Compound(7))

The present invention relates to the compounds of Formula (I) in the forms of a salt, a solvate, a hydrate, an adduct, a complex, a polymorph or a prodrug thereof.

As used herein, the term "$C_1$-$C_6$ alkyl" refers to a straight or branched hydrocarbon group containing 1 to 6 carbon atoms. Examples of $C_1$-$C_6$ alkyl include, but not limited to, methyl, ethyl, n-propyl, isopropyl, tert-butyl, n-pentyl and n-hexyl. The term "$C_1$-$C_6$ alkoxy" refers to an —O—$C_1$-$C_6$ alkyl.

The term "$C_1$-$C_6$ alkylthio" refers to an —S—$C_1$-$C_6$ alkyl.

The term "$C_3$-$C_7$ cycloalkyl" refers to a hydrocarbon radical of saturated cyclic 3-7 membered monocyclic system. Representative examples of $C_3$-$C_7$ cycloalkyl may be cyclopropyl, cyclobutyl, cyclopentyl, cyclohexyl, and cycloheptyl.

The term "halogen", "halo" or "hal" means fluorine, chlorine, bromine or iodine.

The term "aryl" refers to a univalent aromatic hydrocarbyl having 6-20 carbon atoms. Preferably, the aryl group in the present invention contains at most 18, 17, 16, 15, 14, 13, 12, 11 or 10 carbon atoms. The aryl group may be optionally substituted with one or more substituents as defined in the above definition of $R^2$. In one embodiment, 0, 1, 2, 3, 4, 5 or 6 ring atoms of each ring in the aryl group are substituted by a substituent. Examples of the aryl group include, but not limited to, phenyl, naphthyl, anthracenyl, fluorenyl, indenyl and the like, preferably is phenyl or naphthyl.

The term "heteroaryl" refers to a monovalent aromatic radical having one or more carbon atoms and one or more heteroatoms selected from N, O, and S. A heteroaryl group may be a monocyclic heteroaromatic group having 3 to 7 ring members and containing 2 to 6 carbon atoms and 1 to 3 heteroatoms selected from N, O and S or a bicyclic heteroaromatic group having 7 to 10 ring members and containing 4 to 9 carbon atoms and 1 to 3 heteroatoms selected from N, O and S. The heteroaryl group may be optionally substituted with one or more substituents defined in the definition of $R^2$. In one embodiment, 0, 1, 2, 3, or 4 ring atoms in each ring of a heteroaryl group may be substituted. Examples of heteroaryl groups include but not limited to pyridyl, 1-oxo-pyridyl, furanyl, benzo[1,3]dioxolyl, benzo[1,4]dioxinyl thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3] pyrimidinyl, pyrazolo[3,4]pyrimidinyl and benzo(b)thienyl, 3H-thiazolo[2,3-c][1,2,4]thiadiazolyl, imidazo[1,2-d]-1,2,4-thiadiazolyl, imidazo[2,1-b]-1,3,4-thiadiazolyl, 1H,2H-furo[3,4-d]-1,2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c]isoxazolyl, 1H,3H-pyrrolo[1,2-c]oxazolyl, pyrrolo[2,1-b]oxazolyl, and the like.

The term "nitrogen-containing heterocyclic-N-yl" refers to an N-linked saturated or non-aromatic unsaturated monocyclic or bicyclic group having one or more carbon atoms and one or more nitrogen atoms optionally with one or more O or S atoms. The nitrogen-containing heterocyclic-N-yl may be a N-linked monocyclic heterocyclic group having 3 to 7 ring members and containing 2 to 6 carbon atoms and 1 to 3 heteroatoms selected from N, O and S (at least one is N) or a N-linked bicyclic heterocyclic group having 7 to 10 ring members and containing 4 to 9 carbon atoms and 1 to 3 heteroatoms selected from N, O and S (at least one is N). The heterocyclic group may optionally be substituted with one or more substituents as defined in the definition of $R^2$. In one embodiment, 0, 1, 2, 3, or 4 ring atoms in each ring of a heterocyclic group may be substituted with a substituent.

The examples of the N-linked heterocyclic group include but not limited to those linked at position 1 of aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, at position 1 of 1H-indazole, at position 2 of isoindole or isoindoline, at position 4 of morpholine, or at position 9 of carbazole or β-carboline. Still more typically, the N-linked heterocyclic groups include but not limited to 1-aziridyl, 1-azetidyl, 1-pyrrolyl, 1-imidazolyl, 1-pyrazolyl, 1-piperidinyl, and 4-morpholinyl.

The term "substituted" means that one or more substituents (which may be same or different) each replace an H atom.

As used herein, the term "a pharmaceutically acceptable salt of a compound of formula (i)" means an organic acid salt formed with an organic acid which creates a pharmaceutically acceptable anion, the examples include but not limited to, tosylate, methanesulfonate, malate, acetate, citrate, malonate, tartrate, succinate, lactate, benzoate, ascorbate, α-ketoglutarate, and α-glycerophosphate. Suitable inorganic salts may also be formed, including but not limited to, hydrochlorate, sulfate, nitrate, bicarbonate and carbonate, phosphate, hydrobromate, hydriodate salts and the like.

A pharmaceutically acceptable salt may be obtained using standard procedures well known in the art, for example by reacting a sufficient amount of a basic compound with a suitable acid providing a pharmaceutically acceptable anion.

The term "adduct" and "complex" refers to a pharmaceutically acceptable material formed by a compound of the present invention with another small molecule or biological macromolecule via a nonchemical bond.

As used herein, the term "polymorph" means a solid crystalline form of a compound of the present invention or a complex thereof. Various polymorphs of one same compound may exhibit different physical, chemical and/or spectroscopic properties. The different physical properties include, but not limited to, stability (e.g., thermal or light), compressibility and density (which are important for formulation and manufacture of the product), and dissolution rate (which may affect its bioavailability). Differences in stability may result in a change in chemical reactivity (e.g., differential oxidation, such that a dosage form comprised of one polymorph discolors more rapidly than that comprised of another polymorph) or mechanical properties (e.g., in storage, a kinetically favored polymorph in tablet crumble converts to a more thermodynamically stable polymorph) or both (e.g., tablets composed of one polymorph are more susceptible to breakdown at high humidity). Different physical properties of various polymorphs may affect their processing. For example, one polymorph may be more likely to form a solvate or may be more difficult to filter out or remove impurities by washing than another one due to, for example, their particle shape or size distribution.

As used herein, the term "hydrate" means a compound of the present invention or a salt thereof further comprising a stoichiometric or non-stoichiometric amount of water bound via non-covalent intermolecular forces.

As used herein, the term "prodrug" means a derivative of a compound of the invention that can provide a compound of this invention under a biological condition (in vitro or in vivo) via a hydrolyzation, oxidization, or other reactions, unless otherwise indicated. A prodrug may only become active upon such a reaction under a biological condition, or may have activities in its unreacted form. Typically, a prodrug can be prepared using well-known methods, such as those described in BURGER'S MEDICINAL CHEMISTRY AND DRUG DISCOVERY (1995) 172-178, 949-982 (Manfred E. Wolff ed., 5th ed).

The berbamine ring moiety in the compounds of the present invention has the stereochemical structure represented by the structural formula I. The stereochemical definitions and conventions used herein generally follow MCGRAW-HILL DICTIONARY OF CHEMICAL TERMS (S. P. Parker, Ed., McGraw-Hill Book Company, New York, 1984); and ELIEL., E. AND WILEN, S., STEREOCHEMISTRY OF ORGANIC COMPOUNDS (John Wiley & Sons, Inc., New York, 1994). Many organic compounds are present in optically active forms, i.e., they have the ability to rotate a plane of plane-polarized light.

The terms "treatment," "treating," "treat," and the like used herein refer generally to obtaining a desired pharmacological and/or physiological effect. The effect may be prophylactic in terms of completely or partially preventing a disease or symptoms thereof and/or may be therapeutic in terms of partial or complete stabilization or cure of a disease and/or adverse effects caused by the disease. "Treatment" as used herein covers any treatment of a disease in a subject, including: (a) preventing the disease or symptoms from occurring in a subject who is predisposed to the disease or symptoms but has not yet been diagnosed as having it; (b) inhibiting the symptoms of a disease, i.e., arresting its development; or (c) relieving the symptoms of a disease, i.e., causing regression of the disease or symptoms.

The compounds of the present invention can be prepared through a conventional organic chemistry synthesis process. For example, the present invention relates to process for preparing the compound of formula (I):

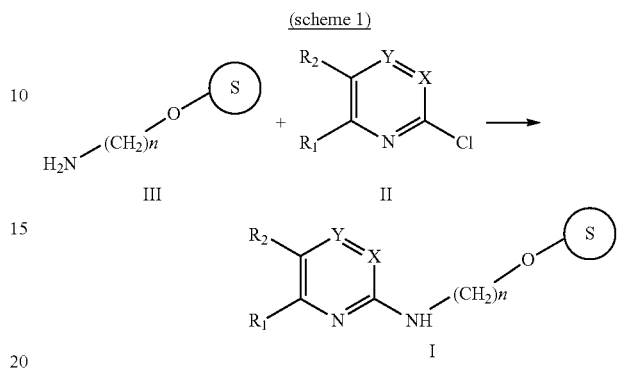

(scheme 1)

wherein the target compound of formula (I) is prepared by conducting an animation reaction of the compound of formula (II) and the compound of formula (III), wherein

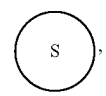

n, X, Y, $R_1$ and $R_2$ in the compounds of formula (II) and (III) are defined same as in the formula (I) above. Said reaction is generally carried out under basic and heated conditions.

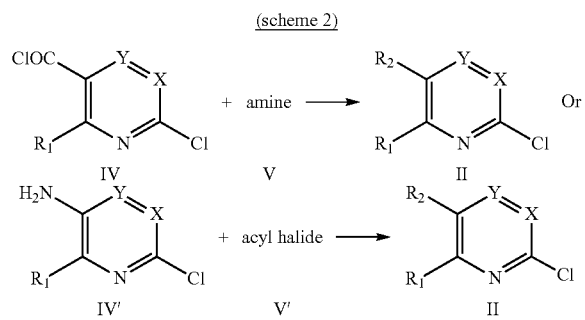

(scheme 2)

The compound of formula (II) is obtained via a nucleophilic substitution reaction between the compound of formula (IV) and the compound of formula (V) or between the compound of formula (IV) and the compound of formula (V'), wherein X, Y, R, and $R_2$ in the compounds of formula (II), (IV) and (IV') are defined same as in the formula (I) above.

The compound of formula (V) is preferably an arylamine, a heteroarylamine or a nitrogen-containing heterocycle optionally substituted with a substituent selected from $C_1$-$C_6$ alkoxy, halogenated $C_1$-$C_6$ alkoxy, $C_1$-$C_6$ alkylthio, halogenated $C_1$-$C_6$ alkylthio, $C_1$-$C_6$ alkyl, halogenated $C_1$-$C_6$ alkyl, $C_3$-$C_7$ cycloalkyl, halogenated $C_3$-$C_7$ cycloalkyl, hydroxyl, halogen, nitro, cyano and amino optionally substituted with one or two $C_1$-$C_6$ alkyl, more preferably is ortho-, para-halogen substituted aniline, meta-alkoxy substituted aniline or morpholine. The preferable examples of the compound of formula (V) are chloro- or fluoro-substituted aniline, methoxy substituted aniline or morpholine.

The compound of formula (V) is preferably an aryl formyl halide, a hetero-aryl formyl halide, or an N-linked nitrogen-containing heterocycle-formyl halide optionally substituted with a substitutent selected from $C_1$-$C_6$ alkoxy, halogenated $C_1$-$C_6$ alkoxy, $C_1$-$C_6$ alkylthio, halogenated $C_1$-$C_6$ alkylthio, $C_1$-$C_6$ alkyl, halogenated $C_1$-$C_6$ alkyl, $C_3$-$C_7$ cycloalkyl, halogenated $C_3$-$C_7$ cycloalkyl, hydroxyl, halogen, nitro, cyano and amino optionally substituted with one or two $C_1$-$C_6$ alkyl, more preferably is ortho- or para-halogen substituted or $C_1$-$C_6$ alkoxy substituted benzoyl halides. The preferable examples of the compound of formula (V') are chloro substituted or methoxy substituted benzoyl chloride.

During this reaction step, generally an excess amount of an amine or organic base is added to neutralize the hydrogen halide generated. The reaction is generally conducted at a low temperature or at room temperature. But for substrate of low activity, heating is needed to promote completion of the reaction.

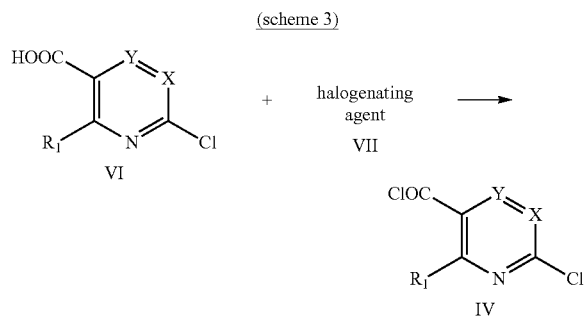

(scheme 3)

The compound of formula (IV) is obtained via a halogen displacement reaction of the hydroxyl group of a carboxyl group between the compound of formula (VI) and the compound of formula (VII), wherein X, Y, and $R_1$ in the compounds of formula (IV) and (VI) are defined same as in the formula (I) above. The compound of formula (VII) is prefebly phosphorus oxychloride ($POCl_3$), sulfoxide chloride ($SOCl_2$), or oxalyl chloride (($COCl)_2$). When the halogenating agent is phosphorus oxychloride ($POCl_3$) or sulfoxide chloride ($SOCl_2$), it should be heated to reflux together with a carboxylic acid; when the halogenating agent is oxalyl chloride (($COCl)_2$), the reation condition may be relatively mild.

Conventional chemical conversion processes may be used to practice this invention. One skilled person in the art would be capable to determine suitable chemical agents, solvents, protecting groups, and reaction conditions for these chemical conversions. Relevant information are described, for example, in R. Larock, *Comprehensive Organic Transformations*, VCH Publishers (1989); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Protecting groups refer to the groups that, upon being attached to an active moiety (e.g., a hydroxyl or amino group), prevent the moiety from interference in a subsequent reaction and, after the reaction, can be removed through a conventional method. Examples of a hydroxyl protecting group include, but not limited to, alkyl, benzyl, allyl, trityl (also known as triphenylmethyl), acyl (e.g., benzoyl, acetyl, or HOOC—X"—CO—, wherein X" is alkylidene, alkenylene, cycloalkylene, or arylene), sityl (e.g., trimethylsily), triethylsilyl, and t-butyldimethylsilyl), alkoxylcarbonyl, aminocarbonyl (e.g., dimethylaminocarbonyl, methylethylaminocarbonyl, and phenylaminocarbonyl), alkoxymethyl, benzyloxymethyl, and alkylmercaptomethyl. Examples of an amino protecting group include, but not limited to, alkoxycarbonyl alkanoyl, aryloxycarbonyl, aryl-substituted alkyl and the like. Hydroxyl and amino protecting groups have been discussed in T. W. Greene and P. G. M. Wuts, Protective Groups in Organic Synthesis, 2nd. Ed., John Wiley and Sons (1991). All hydroxyl and amino protecting groups can be removed by a conventional method after the reaction.

The present invention also provides a pharmaceutical composition comprising the compound of formula (I) of the present invention. The present invention provides a pharmaceutical composition which comprises at least one compound of formula (I) of the present invention as defined above and optionally a pharmaceutically acceptable excipient.

The methods for preparing various pharmaceutical compositions having a certain amount of active components are known or will be apparent to those skilled in the art in light of this disclosure. As described in REMINGTON'S PHARMACEUTICAL SCIENCES, Martin, E. W., ed., Mack Publishing Company, 19th ed. (1995), the methods for preparing such pharmaceutical compositions include incorporation of other suitable pharmaceutical excipients, carriers, diluents, etc.

The pharmaceutical preparations of the present invention are produced by known methods, including routine mixing, dissolving, or lyophilizing processes. The compounds of the present invention may be formulated into a pharmaceutical composition and administered to a patient in a route suitable for the selected administration manner, e.g., orally or parenteraliy (by an intravenous, intramuscular, topical or subcutaneous route).

Thus, the present compounds may be systemically administered, e.g., orally, in conjugation with a pharmaceutically acceptable carrier such as an inert diluent or an assimilable edible carrier. They may be enclosed in hard or soft gelatin capsules, or may be compressed into tablets. For oral therapeutic administration, the active compound may be combined with one or more excipients and may be taken in a form of ingestible tablet, buccal tablet, troche, capsule, elixir, suspension, syrup, wafer, and the like. Such a composition and preparation should contain at least 0.1% of the active compound. This proportion of the compositions and preparations may, of course, vary and may conveniently be from about 1% to about 99% by the weight of a given unit dosage form. The active compound is present in such a therapeutically useful composition in an amount such that an effective dosage level is achieved.

A tablet, troche, pill, capsule and the like may also comprises a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, wintergreen oil, or cherry flavor. When being a capsule as the unit dosage form, it may comprise, in addition to the above material types, a liquid vehicle such as a vegetable oil or polyethylene glycol. Various other materials may be present as coatings or otherwise modify the physical form of the solid unit dosage form. For instance, a tablet, pill, or capsule may be coated with gelatin, wax, shellac or sugar, etc. A syrup or elixir may contain an active compound, a sweetening agent such as sucrose or fructose, a preservative such as methylparaben or propylparaben, a dye and a flavoring agent (such as cherry or orange flavor). Of course, any materials used in preparing any unit dosage form should be pharmaceutically acceptable and substantially non-toxic in the amounts employed. In addition, the active compound may be incorporated into a sustained-release preparation and device.

The active compound may also be administered by infusion or injection intravenously or intraperitoneally. An aqueous solution of the active compound or its salt may be prepared, optionally mixed with a nontoxic surfactant. A dispersion can also be prepared in glycerol, liquid polyethylene glycol, triacetin, and a mixture thereof and in an oil. Under ordinary storage and use conditions, these preparations contain a preservative to prevent the growth of microorganisms.

The pharmaceutical dosage forms suitable for injection or infusion can include a sterile aqueous solution or dispersion or a sterile powder comprising the active ingredient (optionally encapsulated in liposomes) which are adapted for an extemporaneous preparation of a sterile injectable or infusible solution or dispersion. In all cases, the final dosage form must be sterile, liquid and stable under the manufacture and storage conditions. The liquid carrier or vehicle may be a solvent or a liquid dispersion medium comprising, for example, water, ethanol, a polyol (for example, glycerol, propylene glycol, liquid polyethylene glycol, and the like), a vegetable oil, a nontoxic glyceryl ester, and a suitable mixture thereof. The proper fluidity can be maintained, for example, by formation of liposomes, by maintenance of the required particle size in the case of dispersion or by the use of a surfactant. The prevention of microorganism action can be achieved by various antibacterial and antifungal agents, such as parabens, chlorobutanol, phenol, sorbic acid, thimerosal, and the like. In many cases, it will be preferable to include an isotonic agent, such as a sugar, a buffer agent or sodium chloride. Prolonged absorption of an injectable composition can be obtained by the use of a composition of the agents for delaying absorption, for example, aluminum monostearate and gelatin.

A sterile injectable solution is prepared by combining the active compound of a required amount in a suitable solvent with various additional components as listed above as required, followed by biter sterilization. In the case of sterile powder for preparation of a sterile injectable solution, the preferred preparation process is the vacuum drying and lyophilization techniques, which yield a powder of the active ingredient plus any additional desired ingredient present in the previously sterile-filtered solution.

Useful solid carriers include finely divided solids such as talc, clay, microcrystalline cellulose, silica, alumina and the like. Useful liquid carriers include water, ethanol or ethylene glycol or a water-ethanol/ethylene glycol mixture, in which the compound of the present invention can be dissolved or dispersed at an effective level optionally with the aid of a non-toxic surfactant. An adjuvant (such as a flavour) and an additional antimicrobial agent can be added to optimize the properties for a given application.

A thickener material (such as a synthetic polymer, a fatty acid, a fatty acid salt and ester, a fatty alcohol, a modified cellulose or a modified mineral) can also be used with a liquid carrier to form a spreadable paste, gel, ointment, soap and the like for application directly to the skin of a user.

The treatment required amount of the compound or an active salt or derivative thereof will vary depending not only on the selected particular salt but also on the administration route, the nature of the condition to be treated and the age and condition of the patient, and will be ultimately determined at the discretion of the attendant physician or clinician.

The above formulations can present in a unit dosage form which is a physically discrete unit containing a unit dosage suitably administrating to a human or other mammalians. The unit dosage form may be a capsule or a tablet, or a plurality of capsules or tablets. Depending upon the intended particular treatment, the amount of the active ingredient in a unit dosage form can be varied or adjusted in the range of about 0.1 mg to about 1,000 mg or more.

The present invention also provides the use of a compound according to the present invention or a pharmaceutical composition comprising the compound of the present invention in manufacture of a medicament, especially an antitumor medicament. Accordingly, the present invention provides a method for treating a patient suffering from tumor, comprising administrating to the patient in need thereof an therapeuticily effective amount of at least one compound of the present invention. The berbamine derivative of the present invention or a pharmaceutically acceptable salt thereof can be used, for example, for treatment of leukemia, multiple myeloma, lymphoma, liver cancer, gastric cancer, breast cancer, cholangio-cellular carcinoma, pancreatic cancer, lung cancer, carcinoma of large intestine, osteosarcoma, melanoma, cervical cancer, glioma, nasopharyngeal carcinoma, laryngeal carcinoma, esophageal cancer, middle ear tumor, prostate cancer, and so on.

In the following examples, the present invention will be explained more detailedly. However, it should be understood that the following examples are intended to illustrate the present invention but not to limit the scope of the present invention in any way.

The raw chemicals used in the following examples are commercially available or may be obtained by a synthesis method well known the art.

EXAMPLE

Example 1

The Synthesis of Compound (8)

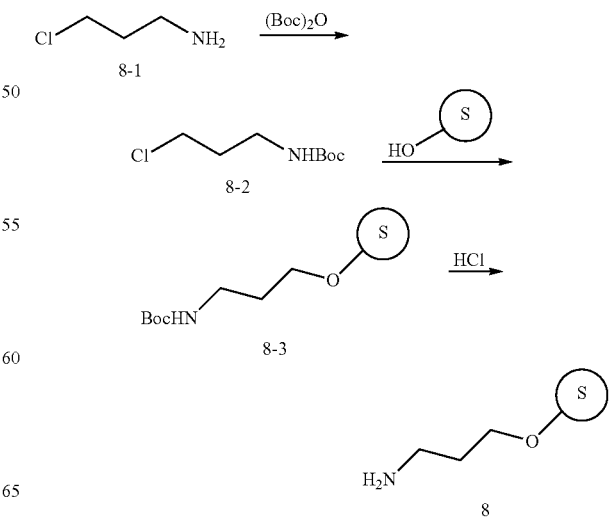

wherein

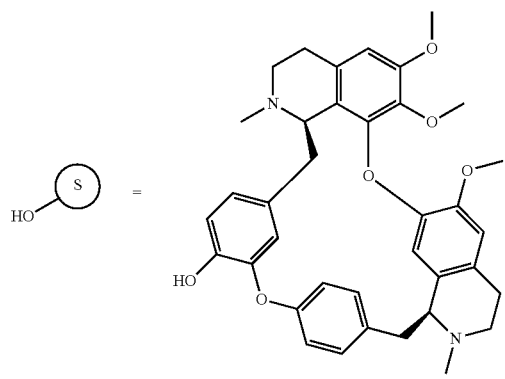

Under stirring, a solution of di-tert-butyl di-carbonate (23.79 g, 110 mmol) in chloroform (50 mL) is slowly added into a solution of 3-chloropropylamine hydrochloride (11.0 g, 110 mmol) and triethylamine (18.42 mL, 130 mmol) in chloroform (50 mL). After stirring overnight at room temperature, a brown oil is obtained as a crude product. Then compound (8-2) (22 g, 95%) as a colorless solid is produced by Kugelrohr distillation at a temperatures of less than 48° C.

Berbamine dihydrochloride (7.0 g, 10.28 mmol) is dissolved in N,N-dimethyl formamide (150 mL). Under nitrogen atmosphere, the solution is cooled to 0° C. After adding NaH (1.65 g, 60%, 41.12 mmol) into the solution, the mixture is stirred for 1 hour, then the solution of compound (8-2) (2.18 g, 11.3 mmol) in N,N-dimethyl formamide (30 mL) is added dropwise therein over 15 minutes. After being stirred for 1 hour at 0° C., the mixture is allowed to be warmed up to room temperature and is stirred for 3 hours, then is heated to 80° C. overnight. After vacuum evaporation, the reaction mixture is diluted with water and extracted with dichloromethane (3*150 mL). The combined organic phase is washed with water and brine, dried through, anhydrous sodium sulfate and filtered. After vacuum concentration, the residue is purified by a preparative high performance liquid chromatography to give compound (8-3) (3.0 g, 38.1%).

Compound (8-3) (3 g, 3.9 mmol) is dissolved in dichloromethane/methanol (50 mL, 10:1). After cooled to 0° C., the solution is added dropwise into a solution of hydrochloric acid in dioxane (4N, 5 mL, 20 mmol) over 10 minutes. Then the solution is warmed up to room temperature and stirred overnight, the reaction mixture is evaporated under vacuum to give compound (8) (2.8 g, 98.6%).

Example 2

The Synthesis of Compound (1)

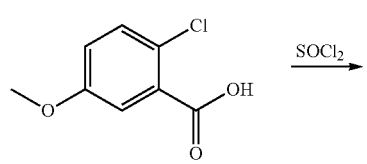

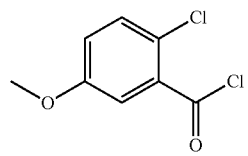

A solution of 2-chloro-5-methoxy benzoic acid (4.0 g, 21.5 mmol) and sulfoxide chloride (2 mL, 27 mmol) in dichloromethane (150 mL) is heated to reflux for 3 hours. The reaction mixture is concentrated to obtain the product. The crude product obtained from the reaction can be directly used for the next step reaction without further purification.

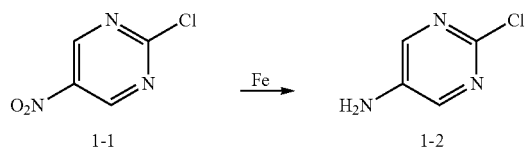

Acetic acid (15 ml., 261 mmol, 8 equivalents) is slowly dripped into a mixture containing iron powder (11 g, 196 mmol, 6 equivalents) and 2-chloro-5-nitro-pyrimidine (5.3 g, 33.33 mmol, 1 equivalent) and methanol (75 mL). After 3 hours, the reaction mixture is diluted with ethyl acetate (300 mL) and filtrated through celite. The organic phase is washed successively with saturated aqueous potassium carbonate solution (200 mL) and brine (200 mL), dried through anhydrous sodium sulfate, and concentrated to give compound (1-2) (2.0 g, 46.4%) as a yellow solid.

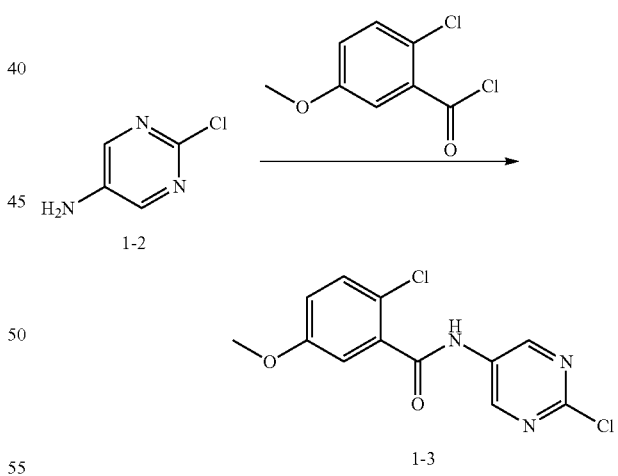

5-Amino-2-chloro pyrimidine (1-2) (2.7 g, 20.6 mmol), 2-chloro-5-methoxy benzoyl chloride (4.2 g, 20.6 mmol) and triethylamine (7 mL) are dissolved in dichloromethane (40 mL). The resultant mixture is stirred overnight at room temperature. After removing the solvent by evaporation, the residue is poured into ethyl acetate and water for extraction separation. The combined organic phase is dried through anhydrous sodium sulfate, concentrated under vacuum, and purified by silica gel column chromatography to give compound (1-3) (5.7 g, 82.6%) as a white solid.

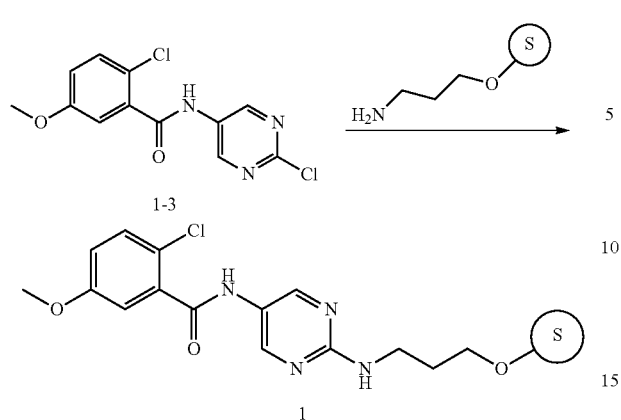

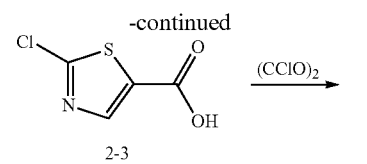

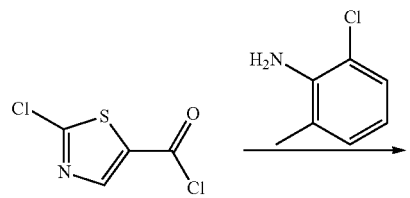

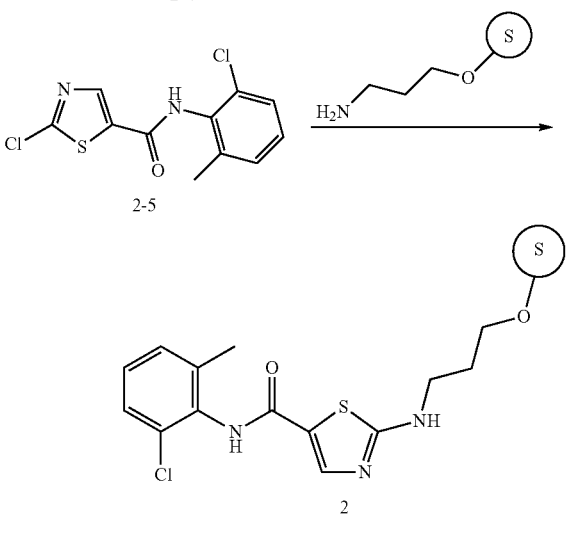

The compound (8) (200 mg, 0.6 mmol) and compound (1-3) (270 mg, 0.90 mmol) are dissolved in N,N-diisopropylethylamine (2 mL), and heated to 110° C. Then the reaction mixture is evaporated under vacuum and purified by a preparative thin layer chromatography to give white or pale yellow compound (1) (16 mg, 2.9%).

LC/MS m/z: M+927.4 100% (purity.).

$^1$H NMR (CDCl$_3$) δ: 8.424 (s, 2H), 7.734 (s, 1H), 7.273~7.253 (m, 2H), 7.210~7.192 (m, 1H), 7.058~7.043 (d, 1H, J=7.5 Hz), 6.902~6.878 (dd, 1H, J=9.0 Hz, 9.0 Hz), 6.769~6.753 (d, 1H, 8.0 Hz), 6.704~6.688 (d, 1H, J=8.0 Hz), 6.588~6.571 (d, 1H, J=8.5 Hz), 6.462 (s, 1H), 6.339 (s, 1H), 6.206 (s, 1H), 5.907 (s, 1H), 5.555~5.534 (t, 1H, J=5.0 Hz, 5.5 Hz), 4.136~4.112 (m, 2H), 3.766 (s, 4H), 3.681 (s, 3H), 3.622~3.584 (dd, 2H, J=12.5 Hz, 12.5 Hz), 3.538 (s, 3H), 3.411 (s, 1H), 3.346~3.299 (m, 1H), 3.226~3.147 (m, 2H), 3.052 (s, 3H), 2.972~2.943 (d, 1H, J=14.5 Hz), 2.884~2.716 (m, 5H), 2.541~2.497 (m, 4H), 2.321~2.302 (m, 1H), 2.184 (s, 3H), 2.133~2.063 (m, 2H).

Example 3

The Synthesis of Compound (2)

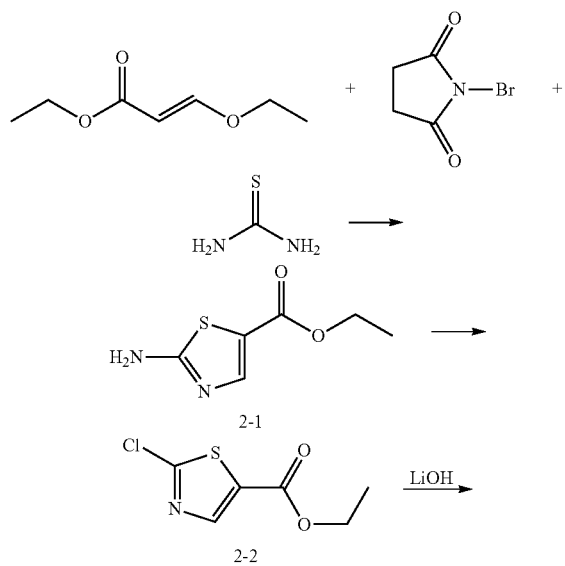

At −10° C., a solution of ethyl 3-ethoxyacrylate (14.4 g, 0.1 mol) in water/dioxane (1:1) (100 mL) is treated with N-bromo-succinimide (19.6 g, 0.11 mol). The reaction mixture is stirred at room temperature for 1 hour, then thiourea (7.6 g, 0.1 mol) is added and the reaction mixture is heated to 80° C. for 1 hour. After the reaction solution is cooled to room temperature, aqueous ammonia (20 mL) is added therein. The paste produced is stirred at room temperature for 10 minutes, and filtered. The resultant filter cake is washed with water and dried under vacuum to give compound (2-1) (12.1 g, 70%).

At 23° C., a solution of ethyl 2-aminothlazole-4-formate (1.0 g, 6.35 mmol) in acetonitrile (10 mL) and tetrahydrofuran (10 mL) is added to a solution (10 mL) of t-butyl nitrite (1.3 mL, 9.52 mmol) and cuprous chloride (1.0 g, 7.6 mmol) in acetonitrile (10 mL) and tetrahydrofuran (10 mL). The reaction mixture is required to be heated at 65° C. until complete consumption of the starting materials as shown by thin-layer chromatography (40% ethyl acetate-hexane). Then, the mixture is cooled to room temperature and partitioned between water and ethyl acetate. The organic layer is concentrated under vacuum and purified by flash silica gel column chromatography eluted with 20% ethyl acetate-hexane to give ethyl 2-chloro-thiazole-4-formate (compound (2-2)) (0.49 g, 40%).

Ethyl 2-chlorothiazole-4-formate (8.8 g, 45 mmol) is dissolved in ethanol (100 mL), and sodium hydroxide (2.13 g, 53.3 mmol) and water (50 mL) are added. After being stirred at room temperature overnight, ethanol is removed under reduced pressure, and the reaction mixture is diluted with water (50 mL). After being washed with ethylether (50 mL), the pH of the mixture is adjusted to about 2 with HCl. The obtained solids are collected through filtration, washed with water and dried to give compound (2-3) (5.12 g, 70%).

At 0° C., oxalyl chloride (2.52 g, 0.02 mol) in dichloromethane (10 mL) is added dropwise into a suspension of 2-chloro-thiazole-5-carboxylic acid (1.64 g, 0.01 mol) and N,N-dimethyl formamide (DMF) (1 drop) in dichloromethane (10 mL), and the mixture is stirred at room temperature overnight. The reaction mixture is evaporated under vacuum, and then the trace amount of oxalyl chloride is removed twice with additional dichloromethane (100 mL) azeotropic mixture to give compound (2-4) (1.82 g, 100%), At 0° C., compound (2-4) (0.91 g, 5 mmol) dissolved in dichloromethane (20 mL) is added into a solution of 2-chloro-6-methyl aniline (0.79 g, 5 mmol) and triethylamine (1.01 g, 10 mmol) in dichloromethane (100 mL), and is stirred at room temperature overnight. The resulting solution is partitioned between dichloromethane and water, The organic layer is dried through anhydrous sodium sulfate and concentrated to give compound (2-5) (0.86 g, 60%).

Compound (8) (200 mg, 0.3 mmol) and compound (2-5) (129 rag, 0.45 mmol) are dissolved in N,N-diisopropyl ethylamine (2 mL), and the solution is heated to 110° C. overnight. Then the reaction mixture is evaporated under vacuum and purified by preparative thin-layer chromatography to give white or pale yellow compound (2) (68.6 mg, 24.9%).

LC/MS m/z: (M+2)/2 458.6 100% (purity), $^1$H NMR (CDCl$_3$) δ: 7.687 (s, 1H), 7.291~7.258 (m, 2H), 7.157~7.102 (m, 4H), 6.909 (s, 1H), 6.821~6.761 (m, 2K), 6.666~6.651 (d, 1H, J=7.5 Hz), 6.528 (s, 1H), 6.401 (s, 1H), 6.277 (s, 1H), 5.972 (s, 1H), 4.240~4.196 (m, 2H), 3.823~3.805 (m, 2H), 3.746 (s, 3H), 3.637~3.578 (m, 5H), 3.386~3.363 (m, 1H), 3.300~3.256 (m, 1H), 3.197~3.158 (m, 1H), 3.114 (s, 3H), 3.034~2.767 (m, 6H), 2.591~2.545 (m, 4H), 2.400~2.361 (m, 1H), 2.275 (s, 3H), 2.237 (s, 2H), 2.197~2.153 (m, 2H), 2.010 (s, 2H).

Example 4

The Synthesis of Compound (3)

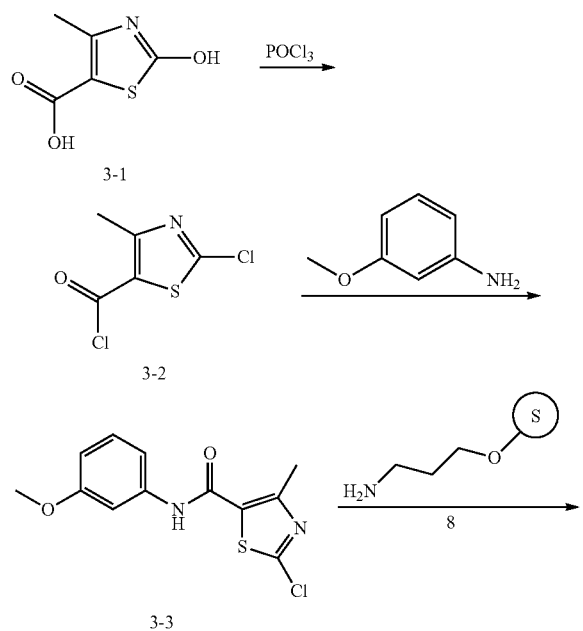

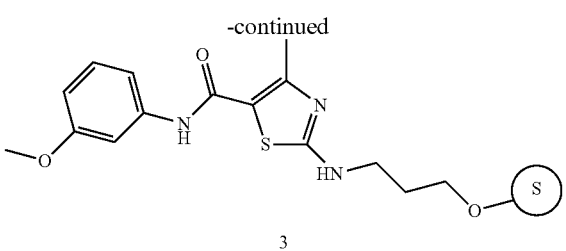

2-Hydroxyl-4-methylthiazole-5-carboxylic acid (10 g, 62.9 mmol) is dissolved in phosphorus oxychloride (50 mL). The reaction mixture is heated under reflux overnight. Then the reaction mixture is evaporated under vacuum to give compound (3-2), which can be directly used for the next step reaction without further purification.

At 0° C., a solution of compound (3-2) in dichloromethane (50 mL) is added dropwise into a solution of 3-methoxy aniline (9.3 g, 75.5 mmol) in dichloromethane (150 mL) over 30 minutes, then the reaction mixture is heated to room temperature overnight. The reaction mixture is diluted with dichloromethane (250 mL). The organic phase is washed with water and brine, dried through anhydrous sodium sulfate and filtered. After being evaporated, the residue is purified by silica gel column chromatography to give compound (3-3) (18.5 g, 89.07%).

Compound (8) (200 mg, 0.3 mmol) and compound (3-3) (129 mg, 0.45 mmol) are dissolved in N,N-diisopropyl ethylamine (2 mL), and the solution is heated to 110° C. overnight. Then the reaction mixture is evaporated under vacuum and purified by preparative thin layer chromatography to give white or pale yellow compound (3) (80.9 mg, 24.9%).

LC/MS m/z: M+912.5 100% (purify).

$^1$H NMR (CDCl$_3$) δ: 9.320 (s, 1H), 7.184~7.247 (m, 2H), 7.099~7.148 (m, 1H), 7.042~7.142 (m, 1H), 6.963~7.001 (m, 1H), 6.794~6.853 (m, 1H), 6.687~6.783 (m, 2H), 6.540~6.611 (m, 1H), 6.431~6.352 (m 1H), 6.182~6.242 (m, 1H), 5.888~5.959 (m, 1H), 4.092~4.183 (m, 2H), 3.770~3.874 (m, 2H), 3.729 (s, 3H), 3.672 (s, 3H), 3.612~3.653 (m, 2H), 3.524 (s, 3H), 3.240~3.460 (m, 3H), 3.134 (s, 3H), 2.982~3.066 (m, 1H), 2.863~2.964 (m, 2H), 2.829~2.933 (m, 4H), 2.500 (s, 3H), 2.449 (s, 3H), 2.185 (s, 3H), 2.041~2.123 (m, 2H).

Example 5

The Synthesis of Compound (4)

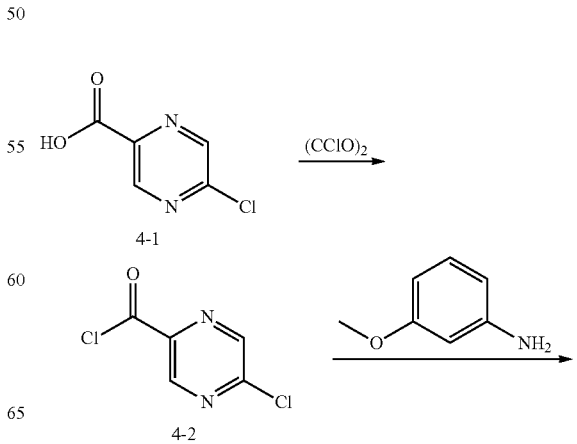

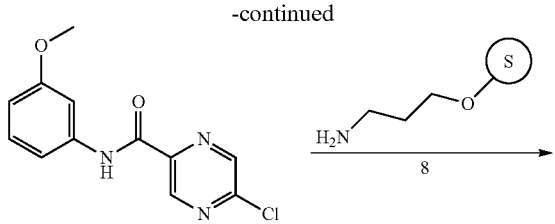

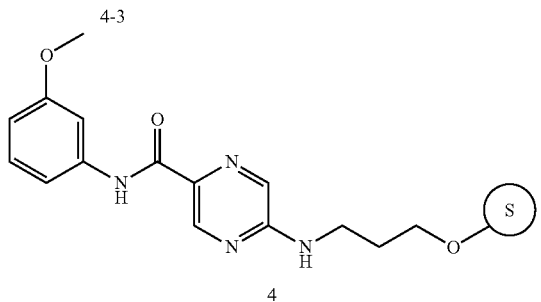

At 0° C., a solution of oxalyl chloride (2.52 g, 0.02 mol) in dichloromethane (10 mL) is dripped dropwise into a suspension of 5-chloropyrazine-2-carboxylic acid (1.56 g, 0.01 mol) and N,N-dimethyl formamide (1 drop) in dichloromethane (100 mL). After being stirred overnight at room temperature, the reaction mixture is evaporated under vacuum, and the trace amount of oxalyl chloride is removed twice by additional dichloromethane (100 mL) azeotropic mixture to give compound (4-2) (1.77 g, 100%), At 0° C., a solution of compound (4-2) (0.89 g. 5 mmol) in dichloromethane (20 mL) is added into a solution of 3-methoxy aniline (0.62 g, 5 mmol) and triethylamine (1.01 g, 10 mmol) in dichloromethane (100 mL) over 30 minutes, and the reaction mixture is heated to room temperature overnight. The reaction mixture is diluted with dichloromethane (100 mL), and the organic phase is washed with water and brine, dried through anhydrous sodium sulfate and filtered. After being evaporated, the residue is purified by silica gel column chromatography to give compound (4-3) (1.1 g, 80%), Under nitrogen atmosphere, $Pd_2(dba)_3$ (2.4 mg, 0.005 equivalent, corresponding to 0.01 equivalent of palladium) and Bippyphos (5.1 mg, 0.02 equivalent, corresponding to a mole ratio of the ligand and palladium of 2:1) in tertiary amyl alcohol (5.0 mL) are charged in a flask, then water (0.10 mL) is added to maintain a homogeneous reaction. The dark purple reaction mixture is stirred for 5-15 minutes, then added with potassium hydroxide (87-89%, particulate) (47.8 mg, 1.5 equivalents) and compound (8) (399.4 mg, 6.00 mmol, 1.2 equivalents), followed by compound (4-3) (0.13 g, 0.50 mmol, 1.0 equivalent). The resulting reaction mixture turned into orange color, and is heated to 100° C. After being stirred for 3 hours, the reaction is cooled to room temperature, and diluted with methyl tert-butyl ether (100 mL) and water (10 mL). The organic layer is dried through anhydrous-sodium sulfate, concentrated under vacuum, and purified by preparative thin layer chromatography to give white or offwhite compound (4) (55.7 mg, 12.5%), LC/MS m/z: (M+2)/2 447.2 100% (purity).

$^1$H NMR (CDCl$_3$) δ: 9.320 (s, 1H), 8.835~8.842 (m, 1H), 7.595~7.605 (m, 1H), 7.540~7.548 (m, 1H), 7.330~7.396 (m, 1H), 7.207~7.258 (m, 2H), 7.112~7.185 (m, 2H), 6.781~6.549 (m, 2H), 6.628~6.728 (m, 3H), 6.419~6.507 (m, 2H), 6.251~6.315 (m, 1H), 4.194~4.320 (m, 2H), 3.770~3.794 (m, 2H), 3.833 (s, 3H), 3.753 (s, 3H), 3.562~3.603 (m, 2H), 3.612 (s, 3H), 3.180~3.420 (m, 3H), 3.334 (s, 3H), 2.942~3.026 (m, 1H), 2.823~2.924 (m, 2H), 2.799~2.893 (m, 4H), 2.587 (s, 3H), 2.202 (s, 3H), 2.144~2.210 (m, 2H).

Example 6

The Synthesis of Compound (5)

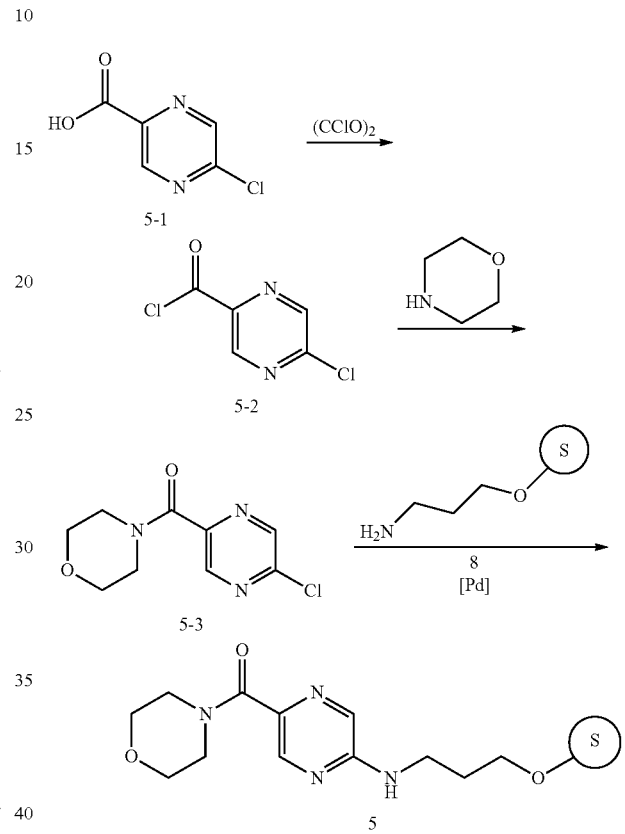

At 0° C., a solution of oxalyl chloride (2.52 g, 0.02 mol) in dichloromethane (10 mL) is added dropwise into a suspension of 5-chloropyrazine-2-carboxylic acid (1.56 g, 0.01 mol) and N,N-dimethyl formamide (1 drop) in dichloromethane (100 mL). After being stirred overnight at room temperature, the reaction mixture is evaporated under vacuum, and the trace amount of oxalyl chloride are removed twice by additional dichloromethane (100 mL) azeotropic mixture to give compound (5-2) (1.77 g, 100%), At 0° C., a solution of compound (5-2) (0.89 g, 5 mmol) in dichloromethane (20 mL) is added into a solution of morpholine (0.44 g, 5 mmol) and triethylamine (1.01 g, 10 mmol) in dichloromethane (100 mL) over 30 minutes, then the reaction mixture is heated to room temperature overnight. The reaction mixture is diluted with dichloromethane (100 mL), and the organic phase is washed with water and brine, dried through anhydrous sodium sulfate and filtered. After being evaporated, the residue is purified by silica gel column chromatography to give compound (5-3) (0.83 g, 73.0%).

Under nitrogen atmosphere, Pd$_2$(dba)$_3$ (2.4 mg, 0.005 equivalent, corresponding to 0.01 equivalent of palladium) and Bippyphos (5.1 mg, 0.02 equivalent, equivalent to a mole ratio of the ligand and palladium of 2:1) in tertiary amyl alcohol (5 mL) are charged in a flask, then water (0.10 mL) is added to maintain a homogeneous reaction. After the dark purple reaction mixture is stirred for 5-15 minutes, potassium hydroxide (87-89%, particulate) (47.8 mg, 1.5 equivalents) and compound (8) (399.4 mg, 6.00 mmol, 1.2 equivalents) are added, followed by compound (5-3) (0.13 g, 0.50 mmol, 1.0 equivalent). After the resulting reaction mixture turned into orange color, it is heated to 100° C. After being stirred for 3 hours, the reaction is cooled to room temperature, and diluted with methyl tert-butyl ether (100 mL) and water (10 mL). The organic layer is dried through anhydrous sodium sulfate, concentrated under vacuum, and purified by preparative thin layer chromatography to give the pale yellow compound (5) (42.9 mg, 10.0%).

LC/MS m/z: M+858.3 100% (purity).

$^1$H NMR (CDCl$_3$) δ: 8.440~8.450 (m, 1H), 7.620~7.630 (m, 1H), 7.300~7.330 (m, 1H), 7.120~7.140 (m, 1H), 6.780~6.830 (m, 2H), 6.650~6.670 (m, 1H), 6.540~7.550 (m, 1H), 6.389~6.460 (m, 1H), 6.249~6.303 (m, 1H), 5.938~6.046 (m, 1H), 4.196~4.302 (m, 2H), 3.820~3.834 (m, 2H), 3.500~3.800 (m, 4H), 3.752 (s, 3H), 3.602~3.643 (m, 2H), 3.609 (s, 3H), 3.180~3.410 (m, 3H), 3.128 (s, 3H), 2.982~3.066 (m, 1H), 2.863~2.964 (m, 2H), 2.759~2.883 (m, 4H), 2.400~2.610 (m, 4H), 2.584 (s, 3H), 2.254 (s, 3H), 2.114~2.198 (m, 2H).

Example 7

The Synthesis of Compound (6)

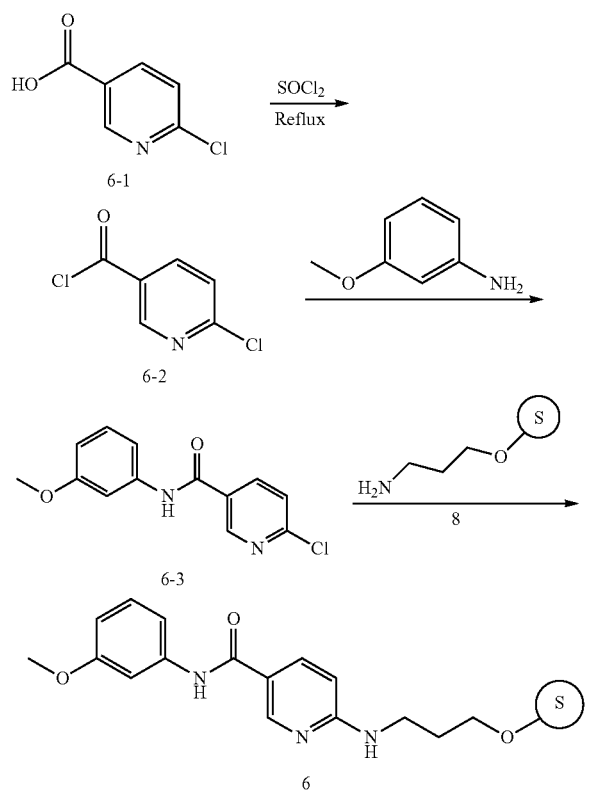

A mixture of 6-chloro-nicotinic acid (5.0 g, 33.8 mmol) in sulfoxide chloride (20 mL) is heated to reflux overnight. The reaction mixture is evaporated under vacuum to give compound (6-2), which can be directly used for the next step reaction without further purification.

At 0° C., a solution of compound (6-2) in dichloromethane (30 mL) is added dropwise into a solution of 3-methoxy aniline (5.5 g, 47.7 mmol) in dichloromethane (150 mL) over 30 minutes, and the reaction mixture is heated to room temperature and stirred overnight. The reaction mixture is diluted with dichloromethane (250 mL), and the organic phase is washed with water and brine, dried through anhydrous sodium sulfate and filtered. After being evaporated, the residue is purified by silica gel column chromatography to give compound (6-3) (7.5 g, 90.0%).

Compound (8) (200 mg, 0.3 mmol) and compound (6-3) (118 mg, 0.45 mmol.) are dissolved in N,N-diisopropyl ethylamine (2 mL), and the solution is heated to 110° C. overnight. Then the reaction mixture is evaporated under vacuum, and purified by preparative thin layer chromatography to give white or offwhite compound (6) (13.0 mg, 4.9%).

LC/MS m/z: M+892.4 100% (purity).

$^1$H NMR (CDCl$_3$) δ: 8.485~8.584 (m, 1H), 7.632~7.650 (m, 1H), 7.540~7.550 (m, 1H), 7.331~7.345 (m, 1H), 7.231~7.253 (m, 1H), 7.146~7.178 (m, 1H), 7.045~7.060 (m, 1H), 6.950~7.060 (m, 1H), 6.739~6.755 (m, 1H), 6.696~6.712 (m, 1H), 6.596~6.636 (m, 2H), 6.460~6.465 (m, 1H), 6.372 (brs, 1H), 6.264~6.282 (m, 1H), 6.210~6.215 (m, 1H), 5.922~6.001 (m, 2H), 4.310~4.144 (m, 2H), 3.770~3.794 (m, 2H), 3.758 (s, 3H), 3.682 (s, 3H), 3.562~3.603 (m, 2H), 3.539 (s, 3H), 3.140~3.370 (m, 3H), 3.054 (s, 3H), 2.942~3.026 (m, 1H), 2.823~2.924 (m, 2H), 2.699~2.823 (m, 4H), 2.502 (s, 3H), 2.378 (s, 3H), 2.054~2.138 (m, 2H).

Example 8

The Synthesis of Compound (7)

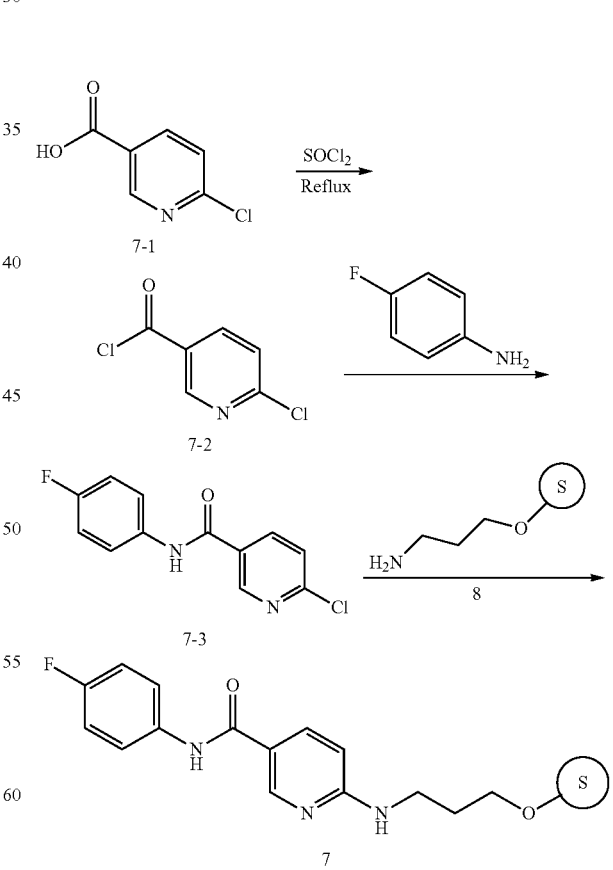

A mixture of 6-chloro-nicotinic acid (5.0 g, 31.8 mmol) in sulfoxide chloride (20 mL) is heated to reflux overnight. The reaction mixture is evaporated under vacuum to give compound (7-2), which can be directly used for the next step reaction without further purification.

At 0° C., a solution of compound (7-2) in dichloromethane (30 mL) is added dropwise into a solution of 4-fluoroaniline (5.3 g, 47.7 mmol) in dichloromethane (150 mL) over 30 minutes, then the reaction mixture is heated to room temperature and stirred overnight. The reaction mixture is diluted with dichloromethane (250 mL). The organic phase is washed with water and brine, dried through anhydrous sodium sulfate and filtered. After being evaporated, the residue is purified by silica gel column chromatography to give compound (7-3) (7.0 g, 88.05%).

Compound (8) (200 mg, 0.3 mmol) and compound (7-3) (118 mg, 0.45 mmol) are dissolved in N,N-diisopropyl ethylamine (2 mL), and the solution is heated to 110° C. Then the reaction mixture is evaporated under vacuum, and purified by preparative thin layer chromatography to give white or off-white compound (7) (10.3 mg, 3.9%).

LC/MS m/z: M+880.4 100% (purity).

$^1$H NMR (CDCl$_3$) δ: 8.554~8.564 (m, 1H), 7.966 (s, 1H), 7.690~7.712 (m, 1H), 7.509~7.537 (m, 2H), 7.283~7.303 (m, 1H), 7.098~7.112 (m, 1H), 6.928~7.010 (m, 2H), 6.759~6.807 (m, 2H), 6.640~6.659 (m, 1H), 6.530~6.480 (m, 1H), 6.430 (brs, 1H), 6.270~6.310 (m, 2H), 5.980~6.050 (m, 2H), 4.178~4.210 (m, 2H), 3.810~3.834 (m, 2H), 3.741 (s, 3H), 3.602~3.643 (m, 2H), 3.609 (s, 3H), 3.180~3.410 (m, 3H), 3.119 (s, 3H), 2.982~3.066 (m, 1H), 2.863~2.964 (m, 2H), 2.739~2.863 (m, 4H), 2.502 (s, 3H), 2.236 (s, 3H), 2.094~2.178 (m, 2H).

Example 9

Evaluation of the Berbamine Derivatives of the Present Invention for their Anti-leukemia Activities (1) Experimental Materials Leukemia cell lines; human K562 leukemia cell line (chronic myeloid leukemia, CML), K562/adr (drug-resistant chronic myeloid leukemia (CML), NB4 (acute promyelocytic leukemia, AML), Kasumi-1 (acute myeloid leukemia M2 type, AML-M2), Jurkat (acute lymphoblastic leukemia, ALL), H9 (acute lymphoblastic leukemia, ALL).

Reagents: The berbamine (BBM) standard is purchased from Sichuan Shifang Pukang Biochemistry Limited Company, Sichuan, China.

The berbamine derivatives according to the present invention:
12-O-(3-(5-(2-chloro-5-methoxy-benzoylamino)-pyrimidin-2-amino)-propyl)-berbamine (compound (1)),
12-O-(3-(5-(2-chloro-6-methyl-phenyl-carbamoyl)-thiazol-2-amino)-propyl)-berbamine (compound (2)),
12-O-(3-(5-(3-methoxy-phenyl-carbamoyl)-4-methyl-thiazol-2-amino)-propyl)-Berbamine (compound (3)),
12-O-(3-(5-(3-methoxy-phenyl-carbamoyl)-pyrazin-2-amino)-propyl)-berbamine (compound (4)),
12-O-(3-(5-(morpholin-4-formyl)-pyrazin-2-amino)-propyl)-berbamine (compound (5)),
12-O-(3-(5-(3-methoxy-phenyl-carbamoyl)-pyridin-2-amino)-propyl)-berbamine (compound (6)),
12-O-(3-(5-(4-fluorophenyl-carbamoyl)-pyridin-2-amino)-propyl)-berbamine (compound (7)).

Main apparatuses: an incubator, and a microplate reader.

(2) Experimental Method

Obtaining 6000 well-growing leukemia cells and inoculating them into wells of a 96-well cell culture plate. The culture medium is the 1640 cell culture medium containing 10% fetal bovine serum. After adding of the berbamine derivatives of different concentrations and mixing uniformly, the plate is placed in a carbon dioxide cell incubator (5% CO$_2$) at 37° C. and incubated for 72 hours. Then the viable cell concentration is determined by the MTT method. In this experiment, the cell viability in control group (not treated with any compound) is set as 100%, and the cell viability (%) after treatment and the 50% inhibiting concentration of the compound for the leukemia cell growth at 72 hours (IC$_{50}$ value of 72 hours) are calculated.

(3) The Experimental Results

The experimental results are shown in table 1. Table 1 shows that the berbamine derivatives of the present invention can induce the death of human chronic myeloid leukemia cells, acme myeloid leukemia cells and acme lymphocytic leukemia cells and inhibit the growth of these leukemia cells. Compared with berbamine itself the berbamine derivatives of the present invention exhibit significantly enhanced anti-leukemia cell activities, wherein the anti-human K562 leukemia cell line (chronic myelogenous leukemia, CML) and anti-human K562 leukemia cell line (chronic myelogenous leukemia, CML) activities of a berbamine derivative of the present invention, compound (3), improve by 8-fold, and the anti-Jurkat acute lymphoblastic leukemia activity of compound (4) improves by more than 13-fold.

Example 10

Evaluation of the Anti-human Multiple Myeloma and Lymphoma Cell Activities of the Berbamine Derivatives of the Present Invention (I) Experimental materials Multiple myeloma and lymphoma cell lines: RPM18226 (multiple myeloma).

Reagents: Same as in Example 9.

Main apparatuses: an incubator, and a microplate reader.

(2) Experimental Method

Obtaining 6000 well-growing abovesaid tumor cells and inoculating them into wells of a 96-well cell culture plate. The culture medium is the 1640 cell culture medium containing 10% fetal bovine serum. After adding the berbamine derivatives of different concentrations and mixing uniformly, the plate is placed in a carbon dioxide cell incubator (5% CO$_2$) at 37° C. and incubated for 72 hours. Then the viable cell concentration is determined by the MTT method. In this experiment, the cell viability of control group (not treated with any compound) is set as 100%, and the cell viability (%) after treatment and the 50% inhibiting concentration of the compound for the leukemia cell growth at 72 hours (IC$_{50}$ value of 72 hours) are calculated.

(3) The Experimental Results

The experimental results are shown in table 1. Table 1 shows that the berbamine derivatives of the present invention can induce the death of human myeloma and lymphoma cells and inhibit the growth of these tumor cells. Compared with berbamine itself, the berbamine derivatives of the present invention exhibit significantly enhanced anti-myeloma and lymphoma cell activities, wherein the berbamine derivative of the present invention, compound (4), improves the anti-RPMI8226 (multiple myeloma) cell line activity by more than 117-fold.

TABLE 1

Determination of the half inhibiting concentrations of the berbamine derivatives on leukemia, lymphoma and multiple myeloma cell growth (72 hours, IC$_{50}$ value)Table 1

|  | K562 | K562adr | NB4 | Kasumi-1 | Jurkat | H9 | RPMI 8226 |
|---|---|---|---|---|---|---|---|
| BBM | 3 | 3.53 | 3 | 1.3 | 1.9 | 5.04 | 1.17 |
| Compound (1) |  | 1.81 |  |  |  |  |  |
| Compound (2) | 0.49 | 0.92 | 1.34 | 0.97 | 0.39 | 1.52 | 0.37 |
| Compound (3) | 0.35 | 0.43 | 0.88 | 0.98 | 0.59 | 2.16 | 0.13 |
| Compound (4) | 0.97 | 0.9 | 1.16 | 1.22 | 0.14 | 0.75 | 0.01 |
| Compound (5) | 1.26 | 1.75 | 3 | 1.21 | 1.79 | 4.25 | 0.30 |
| Compound (6) | 0.82 | 0.58 | 1.15 | 1.33 | 0.97 | 2.24 | 0.08 |
| Compound (7) | 0.95 | 0.64 | 1.43 | 1.15 | 0.84 | 2.36 | 0.10 |

Example 11

Evaluation of Anti-human Solid Tumor Effect of the Berbamine Derivatives of the Present Invention (1) Experimental Materials Human solid tumor cell lines: HepG2 (human hepatocellular carcinoma, HCC), A549 (human lung cancer), MCF-7 (breast cancer), PANC-1 (pancreatic, cancer), PC-3 (prostate cancer). MG63 (osteosarcomas). AGS (gastric cancer), Huh7 (human hepatoma cell), Becap37 (human breast cancer cell), Hela (human cervical cancer cell), RKO (human colon adenocarcinoma cell), SW620 (human colon adenocarcinoma cell), SW480 (human colon cancer cell), MGC 803 (human gastric cancer cell).

Reagents: Same as in Example 9.

Main apparatuses: an incubator, and a microplate reader.

(2) Experimental Method

Obtaining 4000 well-growing human solid tumor cells and inoculating them into wells of a 96-well cell culture plate. The culture medium is DMEM High Glucose cell culture medium containing 10% fetal bovine serum. Alter adding the berbamine derivatives of different concentration and mixing uniformly, the plate is placed in a carbon dioxide cell incubator (5% CO$_2$) at 37° C. and incubated for 72 hours. Then the viable cell concentration is determined by the MTT method, and the cell viability (%) alter drug treatment is calculated. In this experiment, the cell viability of control group (not treated with any compound) is set as 100%.

(3) The Expert Mental Results

The experimental results are shown in table 2. Table 2 shows that the berbamine derivatives of the present invention can induce the death of human solid tumor cells and inhibit the growth of these tumor cells. Compared with berbamine itself, the berbamine derivatives of the present invention exhibit significantly enhanced anti-human solid tumor cell activities, wherein the berbamine derivative of the present invention, compound (4), improves the anti-MCP-7 (breast cancer) cell activity by more than 26-fold, the anti-HepG2 (human hepatocellular carcinoma, HCC) cell activity by about 9-fold, the anti-MGC 803 (human gastric cancer cell) cell activity by more than 8-fold, the anti-SW480 (human colon cancer cell) cell activity by more than 6-fold; the berbamine derivative of the present invention, compound (2), improves the anti-MG63 (osteosarcoma) cell activity by more than 12-fold; and the berbamine derivative of the present invention, compound (6), improves the anti-A549 (human lung cancer) cell activity by more than 14-fold.

TABLE 2

Determination of the half inhibiting concentrations of the berbamine derivatives on human solid tumor cell growth (IC$_{50}$ value, 72 hours)

|  | MCF-7 | A549 | Huh7 | Hepg2 | Becap37 | PANC-1 | Hela |
|---|---|---|---|---|---|---|---|
| BBM | 20.56 | 5.38 | 7.63 | 6.67 | 7.31 | 12.72 | 5.04 |
| Compound (2) | 3.65 | 3.22 | 6 | 2.83 | 2.07 | 1.83 | 1.04 |
| Compound (3) | 3.86 | 1.54 | 3 | 1.41 | 1.04 | 1.06 | 1.3 |
| Compound (4) | 0.77 | 1.39 | 3 | 0.76 | 3.04 | 2.51 | 0.93 |
| Compound (5) | 18.16 | 7.98 | 12 | 9.85 | 9.62 | 8.61 | 6.9 |
| Compound (6) | 3.5 | 0.375 | 6 | 2.61 | 1.52 | 6.85 | 2.12 |
| Compound (7) | 4.45 | 1.84 | 4.05 | 1.65 | 1.42 | 2 | 1.28 |

|  | RKO | SW620 | SW480 | PC-3 | AGS | MG63 | MGC803 |
|---|---|---|---|---|---|---|---|
| BBM | 2.34 | 1.1 | 5.74 | 3.7 | 5.84 | 9.18 | 4.96 |
| Compound (2) | 0.76 | 0.76 | 1.89 | 1.63 | 2.86 | 0.74 | 1.26 |
| Compound (3) | 0.81 | 0.58 | 1.49 | 1.41 | 1.87 | 1.25 | 0.68 |
| Compound (4) | 0.78 | 0.29 | 0.91 | 1.04 | 1.38 | 1.23 | 0.62 |
| Compound (5) | 2.07 | 1.89 | 5.75 | 7.47 | 8.29 | 6.67 | 5.56 |
| Compound (6) | 1.02 | 1.26 | 1.56 | 2.92 | 2.55 | 1.3 | 1.2 |
| Compound (7) | 1.42 | 0.74 | 2 | 3.27 | 3.12 | 1.3 | 1.29 |

The invention claimed is:

1. A berbamine derivative of formula (I)

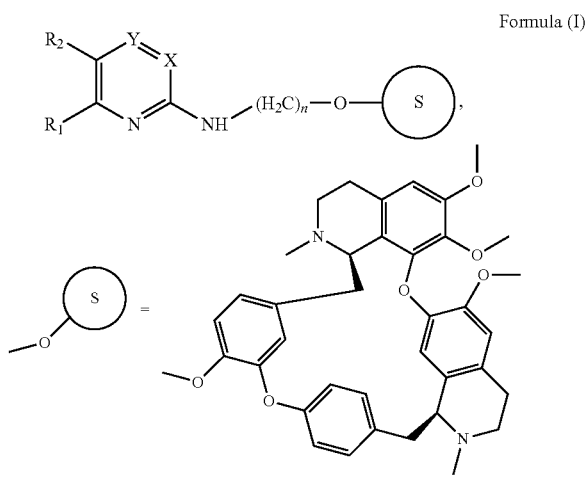

Formula (I)

wherein, n=1-15;

R$_1$ is selected from H, C$_1$-C$_6$ alkoxy, halogenated C$_1$-C$_6$ alkoxy, C$_1$-C$_6$ alkylthio, halogenated C$_1$-C$_6$ alkylthio, C$_1$-C$_6$ alkyl, halogenated C$_1$-C$_6$ alkyl, C$_3$-C$_7$ cycloalkyl, halogenated $C_3$-$C_7$ cycloalkyl, halogen, nitro, cyano and amino optionally substituted with one or two $C_1$-$C_6$ alkyl;

$R_2$ is selected from aryl carbamoyl, aryl carbonyl amino, heteroaryl carbamoyl, heteroaryl carbonyl amino, and N-linked nitrogen-containing heterocycle-carbonyl optionally substituted with a substituent selected from $C_1$-$C_6$ alkoxy, halogenated $C_1$-$C_6$ alkoxy, $C_1$-$C_6$ alkylthio, halogenated $C_1$-$C_6$ alkylthio, $C_1$-$C_6$ alkyl, halogenated $C_1$-$C_6$ alkyl, $C_3$-$C_7$ cycloalkyl, halogenated $C_3$-$C_7$ cycloalkyl, hydroxyl, halogen, nitro, cyano and amino optionally substituted with one or two $C_1$-$C_6$ alkyl;

X, Y are absent, CH, N or S, provided that X and Y cannot be absent at the same time;

or a pharmaceutically acceptable salt thereof.

2. The berbamine derivative or a pharmaceutically acceptable salt thereof according to claim 1, wherein n is an integer of 1-10.

3. The berbamine derivative or a pharmaceutically acceptable salt thereof according to claim 1, wherein n is an integer of 1-7.

4. The berbamine derivative or a pharmaceutically acceptable salt thereof according to claim 1, wherein n is an integer of 3-5.

5. The berbamine derivative or a pharmaceutically acceptable salt thereof according to claim 1, wherein $R_1$ is H, $C_1$-$C_6$ alkoxy, $C_1$-$C_6$ alkylthio, $C_1$-$C_6$ alkyl, $C_3$-$C_7$ cycloalkyl, halogen, nitro, cyano and amino optionally substituted with one or two $C_1$-$C_6$ alkyl.

6. The berbamine derivative or a pharmaceutically acceptable salt thereof according to claim 1, wherein $R_1$ is H, $C_1$-$C_6$ alkoxy, $C_1$-$C_6$ alkyl, $C_3$-$C_7$ cycloalkyl or halogen.

7. The berbamine derivative or a pharmaceutically acceptable salt thereof according to claim 1, wherein $R_1$ is H, $C_1$-$C_3$ alkoxy, $C_1$-$C_3$ alkyl, or $C_5$-$C_6$ cycloalkyl.

8. The berbamine derivative or a pharmaceutically acceptable salt thereof according to claim 1, wherein $R_1$ is H, methoxy, or methyl.

9. The berbamine derivative or a pharmaceutically acceptable salt thereof according to claim 1, wherein $R_1$ is H.

10. The berbamine derivative or a pharmaceutically acceptable salt thereof according to claim 1, wherein $R_2$ is aryl carbamoyl, aryl carbonyl amino, heteroaryl carbamoyl, heteroaryl carbonyl amino, or N-linked nitrogen-containing heterocycle-carbonyl optionally substituted with a substituent selected from $C_1$-$C_6$ alkoxy, $C_1$-$C_6$ alkylthio, $C_1$-$C_6$ alkyl, $C_3$-$C_7$ cycloalkyl, hydroxyl, halogen, nitro, cyano and amino optionally substituted with one or two $C_1$-$C_6$ alkyl.

11. The berbamine derivative or a pharmaceutically acceptable salt thereof according to claim 1, wherein $R_2$ is aryl carbamoyl, aryl carbonyl amino, heteroaryl carbamoyl, heteroaryl carbonyl amino, or N-linked nitrogen-containing heterocycle-carbonyl optionally substituted with a substituent selected from $C_1$-$C_3$ alkoxy, $C_1$-$C_3$ alkyl, $C_5$-$C_6$ cycloalkyl, hydroxyl, halogen, nitro, cyano and amino optionally substituted with one or two $C_1$-$C_3$ alkyl.

12. The berbamine derivative or a pharmaceutically acceptable salt thereof according to claim 1, wherein $R_2$ is aryl carbamoyl, aryl carbonyl amino, heteroaryl carbamoyl, heteroaryl carbonyl amino, or N-linked nitrogen-containing heterocycle-carbonyl optionally substituted with a substituent selected from $C_1$-$C_3$ alkoxy and halogen.

13. The berbamine derivative or a pharmaceutically acceptable salt thereof according to claim 1, wherein $R_2$ is aryl carbamoyl, aryl carbonyl amino, heteroaryl carbamoyl, heteroaryl carbonyl amino, or N-linked nitrogen-containing heterocycle-carbonyl optionally substituted with a substitute selected from methoxy, Cl and F.

14. The berbamine derivative or a pharmaceutically acceptable salt thereof claim 1, wherein $R_2$ is phenyl carbamoyl, phenyl carbonyl amino, or morpholin-4-yl carbonyl optionally substituted with a substituent selected from methoxy, Cl and F.

15. The berbamine derivative or a pharmaceutically acceptable salt thereof according to claim 1, wherein X=N, and Y=CH.

16. The berbamine derivative or a pharmaceutically acceptable salt thereof according to claim 1, wherein X=S, and Y is absent.

17. The berbamine derivative or a pharmaceutically acceptable salt thereof according to claim 1, wherein X=CH, and Y=N.

18. The berbamine derivative or a pharmaceutically acceptable salt thereof according to claim 1, wherein X=CH, and Y=CH.

19. The berbamine derivative or a pharmaceutically acceptable salt thereof according to claim 1, selected from the following compounds:

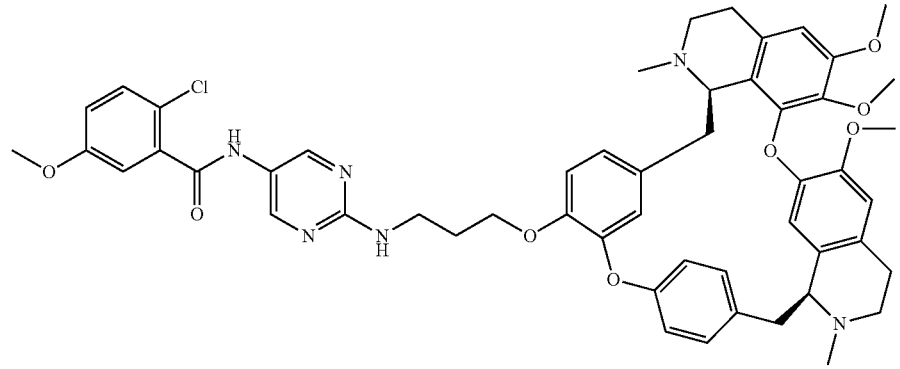

-continued
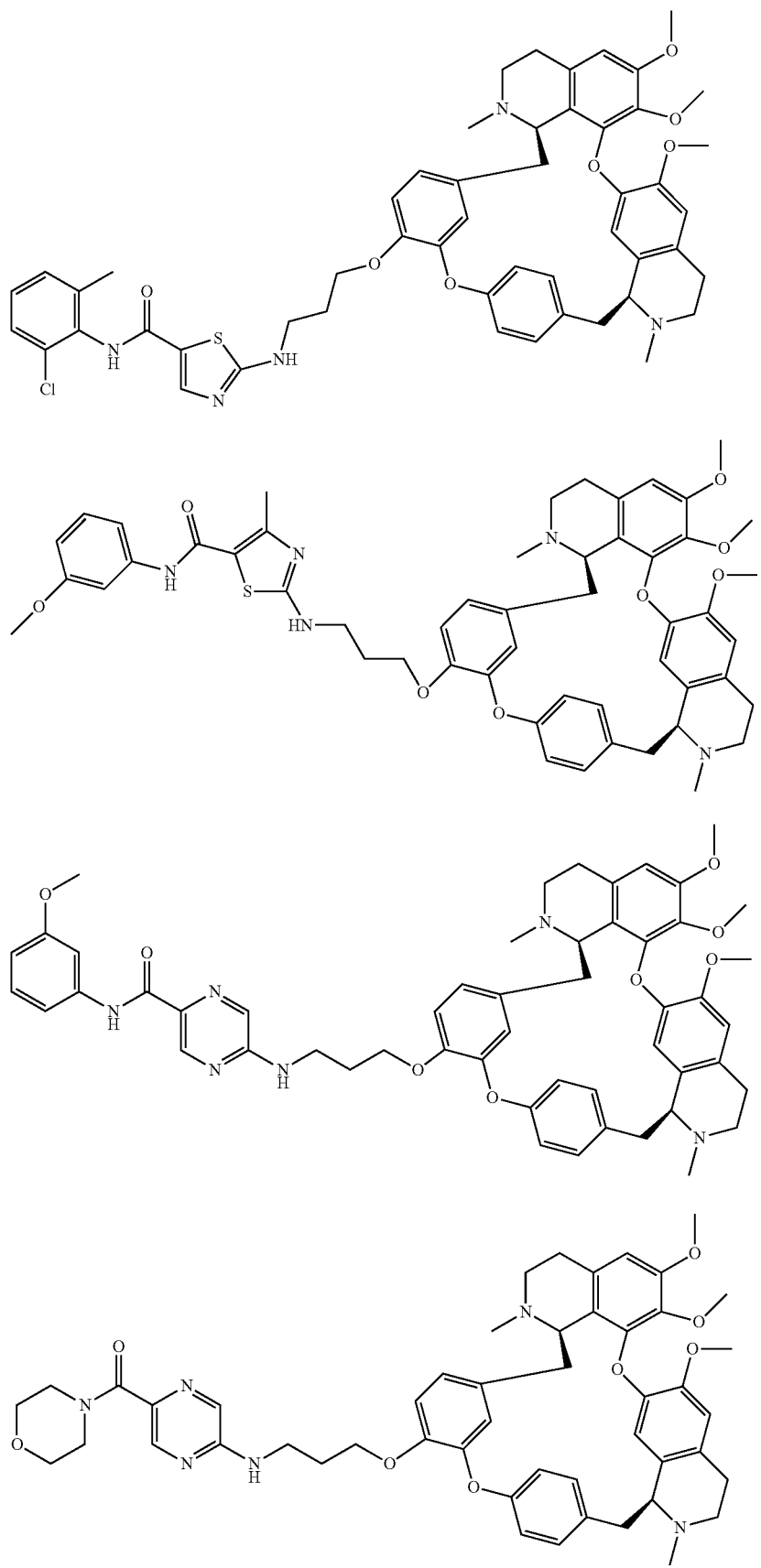

-continued

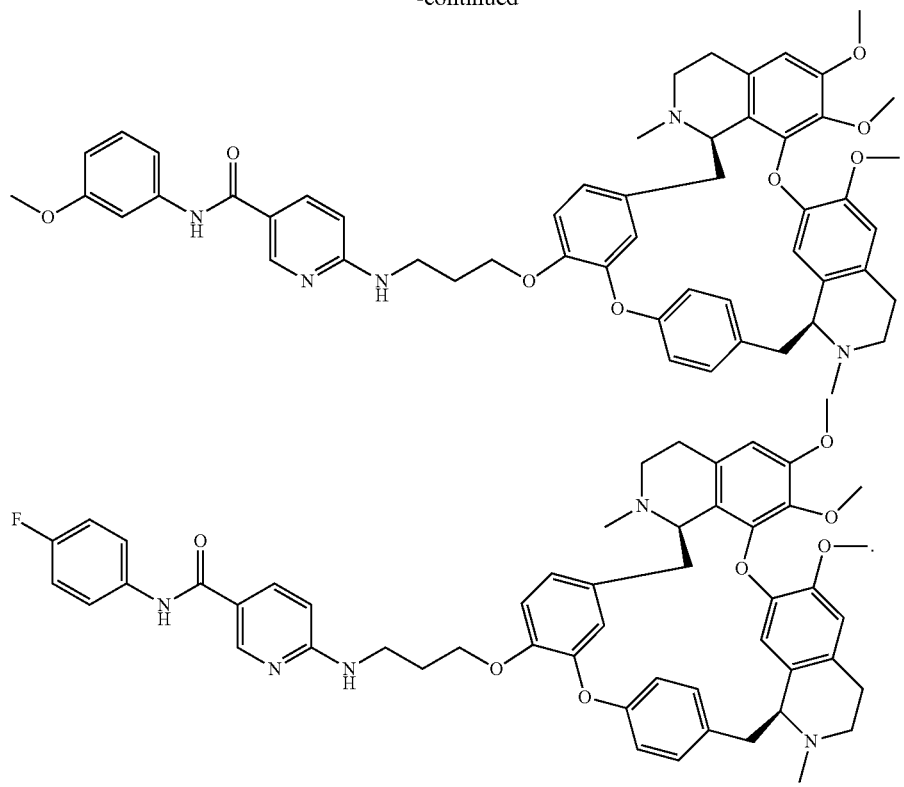

20. A process for preparing the compound of formula I,

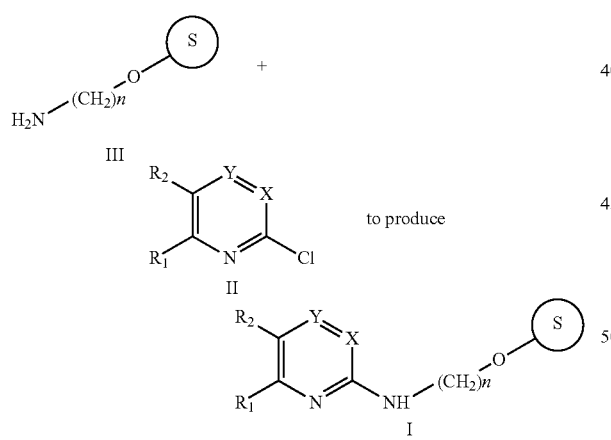

comprising conducting an amination reaction of the compound of formula (III) and the compound of formula (II) to produce a compound of formula (I), wherein n, X, Y, $R_1$ and $R_2$ in the compounds of formula (I), (II) and (III) are defined same as in claim 1.

21. The process according to claim 20, wherein the compound of formula (II) is obtained via a nucleophilic substitution reaction between the compound of formula (IV) and the compound of formula (V) or between the compound of formula (IV') and the compound of formula (V'),

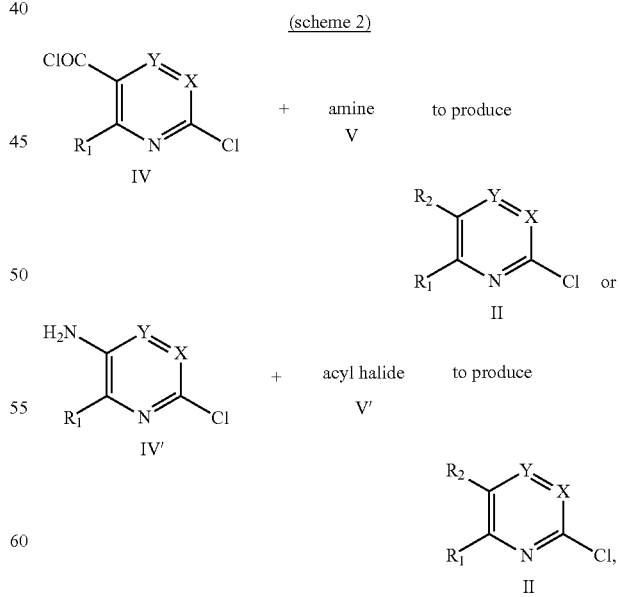

wherein X, Y, $R_1$ and $R_2$ in the compounds of formula (II), (IV) and (IV') are defined same as in claim 1.

22. The process according to claim 21, wherein the compound of formula (V) is arylamine, heteroarylamine or nitrogen-containing heterocycle optionally substituted with a substituent selected from $C_1$-$C_6$ alkoxy, halogenated $C_1$-$C_6$ alkoxy, $C_1$-$C_6$ alkylthio, halogenated $C_1$-$C_6$ alkylthio, $C_1$-$C_6$ alkyl, halogenated $C_1$-$C_6$ alkyl, $C_3$-$C_7$ cycloalkyl, halogenated $C_3$-$C_7$ cycloalkyl, hydroxyl, halogen, nitro, cyano and amino optionally substituted with one or two $C_1$-$C_6$ alkyl, and the compound of formula (V') is aryl formyl halide, heteroaryl formyl halide, or N-linked nitrogen-containing heterocycle-formyl halide optionally substituted with a substitutent selected from $C_1$-$C_6$ alkoxy, halogenated $C_1$-$C_6$ alkoxy, $C_1$-$C_6$ alkylthio, halogenated $C_1$-$C_6$ alkylthio, $C_1$-$C_6$ alkyl, halogenated $C_1$-$C_6$ alkyl, $C_3$-$C_7$ cycloalkyl, halogenated $C_3$-$C_7$ cycloalkyl, hydroxyl, halogen, nitro, cyano and amino optionally substituted with one or two $C_1$-$C_6$ alkyl.

23. The process according to claim 21, wherein the compound of formula (V) is ortho- or para-halogen substituted aniline, meta-alkoxy substituted aniline or morpholine, and the compound of formula (V') is ortho- or para-halogen substituted, or $C_1$-$C_6$ alkoxy substituted benzoyl halide.

24. The process according to claim 21, wherein the compound of formula (V) is chloro- or fluoro-substituted aniline, methoxy substituted aniline or morpholine, and the compound of formula (V') is chloro substituted or methoxy substituted benzoyl chloride.

25. The process according to claim 21, wherein compound of formula (IV) is obtained via a halogen displacement reaction of the hydroxyl group of a carboxyl group between a carboxylic acid (VI) and a compound of formula (VII),

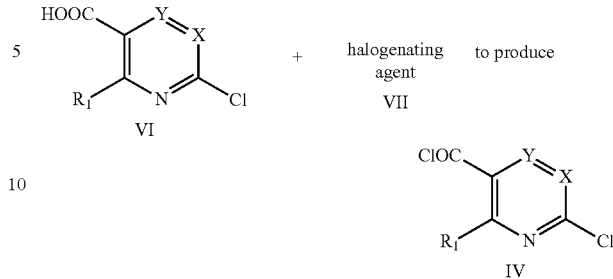

wherein X, Y and $R_1$ in the compounds of formula (VI) and (IV) are defined same as in claim 1.

26. The process according to claim 25, wherein the halogenating agent of formula (VII) is phosphorus oxychloride ($POCl_3$), sulfoxide chloride ($SOCl_2$), or oxalyl chloride (($COCl)_2$).

27. A pharmaceutical composition, comprising the berbamine derivative or a pharmaceutically acceptable salt thereof according to claim 1 and optionally a pharmaceutically acceptable excipient.

* * * * *

UNITED STATES PATENT AND TRADEMARK OFFICE
CERTIFICATE OF CORRECTION

| | |
|---|---|
| PATENT NO. | : 8,987,288 B2 |
| APPLICATION NO. | : 13/821667 |
| DATED | : March 24, 2015 |
| INVENTOR(S) | : Xu et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 221 days.

Signed and Sealed this
Thirteenth Day of October, 2015

Michelle K. Lee
*Director of the United States Patent and Trademark Office*